A US011331327B2

(12) United States Patent
Delavenne et al.

(10) Patent No.: US 11,331,327 B2
(45) Date of Patent: *May 17, 2022

(54) ANTIBACTERIAL USE OF HALOGENATED SALICYLANILIDES

(71) Applicant: UNION therapeutics A/S, Hellerup (DK)

(72) Inventors: Emilie Flora Aurore Delavenne, Le Mans (FR); Daniel Jean Jacques Simon, Søborg (DK); Morten Otto Alexander Sommer, Virum (DK); Rasmus Vendler Toft-Kehler, Copenhagen Ø (DK)

(73) Assignee: UNION therapeutics A/S, Hellerup (DK)

(*) Notice: Subject to any disclaimer, the term of this patent is extended or adjusted under 35 U.S.C. 154(b) by 0 days.

This patent is subject to a terminal disclaimer.

(21) Appl. No.: 16/899,821

(22) Filed: Jun. 12, 2020

(65) Prior Publication Data

US 2020/0306270 A1  Oct. 1, 2020

Related U.S. Application Data

(63) Continuation of application No. 16/125,511, filed on Sep. 7, 2018, now Pat. No. 10,758,553, which is a continuation of application No. 15/510,304, filed as application No. PCT/EP2015/070495 on Sep. 8, 2015, now abandoned.

(30) Foreign Application Priority Data

Sep. 12, 2014 (SE) .................................. 1451054-9

(51) Int. Cl.
| | |
|---|---|
| A61K 31/609 | (2006.01) |
| A61K 9/00 | (2006.01) |
| A61K 47/10 | (2017.01) |
| A61K 47/14 | (2017.01) |
| A61K 47/26 | (2006.01) |
| A61K 9/06 | (2006.01) |
| A61P 31/04 | (2006.01) |
| A61P 17/00 | (2006.01) |

(52) U.S. Cl.
CPC .......... *A61K 31/609* (2013.01); *A61K 9/0014* (2013.01); *A61K 9/06* (2013.01); *A61K 47/10* (2013.01); *A61K 47/14* (2013.01); *A61K 47/26* (2013.01); *A61P 17/00* (2018.01); *A61P 31/04* (2018.01)

(58) Field of Classification Search
CPC ......... A61K 31/609; A61P 17/00; A61P 31/04
See application file for complete search history.

(56) References Cited

U.S. PATENT DOCUMENTS

| | | | |
|---|---|---|---|
| 2,731,386 A | 1/1956 | Reiner | |
| 3,152,039 A | 10/1964 | Mattson | |
| 3,674,850 A | 7/1972 | Osborne | |
| 3,914,418 A | 10/1975 | Patchett et al. | |
| 4,287,191 A | 9/1981 | Coburn et al. | |
| 4,310,682 A | 1/1982 | Ozawa et al. | |
| 4,358,443 A | 11/1982 | Coburn et al. | |
| 4,671,957 A | 6/1987 | Holtshousen | |
| 4,742,083 A | 5/1988 | Ritchey | |
| 4,883,660 A | 11/1989 | Blackman et al. | |
| 4,939,132 A | 7/1990 | Coburn et al. | |
| 5,958,911 A | 9/1999 | Evans et al. | |
| 6,117,859 A | 9/2000 | Evans et al. | |
| 6,251,869 B1 | 6/2001 | Bohanon | |
| 6,399,629 B1 | 6/2002 | Chamberland et al. | |
| 6,492,425 B1 | 12/2002 | Callahan et al. | |
| 6,534,489 B1 | 3/2003 | Jomaa | |
| 6,830,758 B2 | 12/2004 | Nichols et al. | |
| 8,097,759 B2 | 1/2012 | Muto et al. | |
| 8,198,326 B2 | 6/2012 | Scholz | |
| 8,263,657 B2 | 9/2012 | Muto et al. | |
| 8,846,646 B2 | 9/2014 | Chiou | |
| 9,446,131 B2 | 9/2016 | Hardas et al. | |
| 9,949,988 B2 * | 4/2018 | Delavenne | A61K 31/609 |
| 10,463,680 B2 | 11/2019 | Sommer et al. | |
| 10,758,553 B2 | 9/2020 | Delavenne et al. | |
| 10,857,164 B2 | 12/2020 | Sommer et al. | |
| 11,045,434 B1 | 6/2021 | Sommer et al. | |

(Continued)

FOREIGN PATENT DOCUMENTS

| | | |
|---|---|---|
| CA | 2344867 | 3/2000 |
| CA | 2360661 | 8/2000 |

(Continued)

OTHER PUBLICATIONS

"Study ATx201-004, Ointment 2% or 4% in Impetigo," 2 pages.
Akiyama et al., "Recent Investigations of *Staphylococcus aureus* in Dermatology," Nippon Hifuka Gakkai Zasshi, 109(13), 2095-2102 (Abstract Only) (1999).
Andrews, et al., The Biology and Toxicology of Molluscicides, Bayluscide®, Pharmac. Ther. 1983, pp. 245-295, vol. 19.
Beers, et al., The Merck Manual of Medical Information, Second Home Edition, 2003, pp. 1222-1223.
Bieber, "Atopic dermatitis," N. Engl. J. Med., 358, pp. 1483-1494 (2008).

(Continued)

*Primary Examiner* — Kevin E Weddington
(74) *Attorney, Agent, or Firm* — Mintz Levin Cohn Ferris Glovsky and Popeo, P.C.

(57) ABSTRACT

The invention relates to a halogenated salicylanilide selected from closantel, rafoxanide, oxyclozanide and niclosamide and derivatives thereof including salts, hydrates, esters and the like for use in the topical treatment or prevention of infections caused by Gram-positive bacteria such as *Staphylococcus*, in particular *Staphylococcus aureus*, and *Streptococcus*, in particular *Streptococcus pyogenes*. Grain positive bacteria treated with the halogenated salicylanilides exhibit a very low frequency of appearance of resistant mutants compared to commonly used topical antibiotics.

6 Claims, 5 Drawing Sheets

(56) References Cited

U.S. PATENT DOCUMENTS

| | | |
|---|---|---|
| 2002/0192273 A1 | 12/2002 | Buseman et al. |
| 2003/0036533 A1 | 2/2003 | Jomaa |
| 2003/0045746 A1 | 3/2003 | Jomaa |
| 2004/0071757 A1 | 4/2004 | Rolf |
| 2004/0082549 A1 | 4/2004 | Jomaa |
| 2005/0075511 A1 | 4/2005 | Jomaa |
| 2006/0052452 A1 | 3/2006 | Scholz |
| 2006/0280783 A1 | 12/2006 | Dipietro et al. |
| 2007/0059351 A1 | 3/2007 | Murrell et al. |
| 2010/0029781 A1 | 2/2010 | Morris |
| 2010/0317643 A1 | 12/2010 | Goodacre et al. |
| 2013/0005802 A1 | 1/2013 | Chen et al. |
| 2013/0189368 A1 | 7/2013 | Mosqueira et al. |
| 2014/0135296 A1 | 5/2014 | Deretic et al. |
| 2014/0294957 A1 | 10/2014 | Stein et al. |
| 2015/0104492 A1 | 4/2015 | McDermott et al. |
| 2015/0250808 A1 | 9/2015 | Deretic et al. |
| 2016/0143987 A1 | 5/2016 | Engelthaler et al. |
| 2016/0199343 A1 | 7/2016 | De Visscher et al. |
| 2016/0303034 A1 | 10/2016 | Collins et al. |
| 2017/0014325 A1 | 1/2017 | Carola et al. |
| 2017/0056347 A1 | 3/2017 | Glick et al. |
| 2017/0172943 A1 | 6/2017 | Hardas et al. |
| 2017/0258816 A1 | 9/2017 | Delavenne et al. |
| 2017/0304372 A1 | 10/2017 | Kim et al. |
| 2018/0207179 A1 | 7/2018 | Sommer et al. |
| 2018/0224470 A1 | 8/2018 | Leung et al. |
| 2019/0151231 A1 | 5/2019 | Sommer et al. |
| 2019/0201422 A1 | 7/2019 | Sommer et al. |
| 2020/0268693 A1 | 8/2020 | Mylonakis et al. |
| 2020/0306270 A1 | 10/2020 | Delavenne et al. |
| 2020/0306271 A1 | 10/2020 | Delavenne et al. |
| 2021/0137948 A1 | 5/2021 | Sommer |
| 2021/0308153 A1 | 10/2021 | Sommer et al. |

FOREIGN PATENT DOCUMENTS

| | | |
|---|---|---|
| CA | 2399947 | 8/2001 |
| CN | 104053632 A | 9/2014 |
| CN | 104430338 A | 3/2015 |
| DE | 19828097 | 12/1999 |
| DE | 19843334 | 3/2000 |
| DE | 19843360 | 3/2000 |
| DE | 19843383 | 3/2000 |
| DE | 19859426 A1 | 7/2000 |
| EP | 0221211 | 5/1987 |
| EP | 0487973 | 6/1992 |
| EP | 1140952 | 10/2001 |
| EP | 1174439 | 1/2002 |
| EP | 1514544 | 3/2005 |
| EP | 3020398 | 5/2016 |
| FR | 1340175 A | 10/1963 |
| GB | 1421589 A | 1/1976 |
| GB | 1527638 A | 10/1978 |
| GB | 2456376 A | 7/2009 |
| GB | 2465633 A | 6/2010 |
| JP | 2004-331577 A | 11/2004 |
| JP | 2007007189 A | 1/2007 |
| JP | 2009-519709 A | 5/2009 |
| JP | 2010-528098 A | 8/2010 |
| JP | 2011-511774 A | 4/2011 |
| JP | 2012-012338 A | 1/2012 |
| JP | 2012-0505867 A | 3/2012 |
| JP | 2013-529668 A | 7/2013 |
| RU | 2227025 C2 | 4/2004 |
| SU | 597671 | 3/1978 |
| WO | 9619220 A1 | 6/1996 |
| WO | WO-1998/056390 | 5/1998 |
| WO | 9965449 A2 | 12/1999 |
| WO | WO-2000/004031 | 1/2000 |
| WO | WO-2000/016757 | 3/2000 |
| WO | WO-2000/017212 | 3/2000 |
| WO | WO-2000/044359 | 8/2000 |
| WO | WO-2000/048636 | 8/2000 |
| WO | WO-2001-60157 | 8/2001 |
| WO | WO-2001/093872 | 12/2001 |
| WO | WO-2002-45662 | 6/2002 |
| WO | WO-2003-072113 | 9/2003 |
| WO | 03103665 A1 | 12/2003 |
| WO | WO-2004/006906 | 1/2004 |
| WO | WO-2004/047842 | 6/2004 |
| WO | WO-2004/062600 | 7/2004 |
| WO | WO-2005/025598 | 3/2005 |
| WO | WO-2005/074912 | 8/2005 |
| WO | WO-2006/104763 | 10/2006 |
| WO | WO-2007/066130 | 6/2007 |
| WO | 2007119151 A1 | 10/2007 |
| WO | 2008006848 A1 | 1/2008 |
| WO | WO-2008/021088 | 2/2008 |
| WO | WO-2008/092006 | 7/2008 |
| WO | WO-2008/133982 | 11/2008 |
| WO | WO-2008/155535 | 12/2008 |
| WO | 2009111040 A1 | 9/2009 |
| WO | WO-2009/111040 | 9/2009 |
| WO | WO-2009/140215 | 11/2009 |
| WO | 2010003568 A1 | 1/2010 |
| WO | WO-2010/005836 | 1/2010 |
| WO | WO-2010/043717 | 4/2010 |
| WO | WO-2010/061330 | 6/2010 |
| WO | WO-2010/129062 | 11/2010 |
| WO | WO-2011/098579 | 8/2011 |
| WO | WO-2012/032360 | 3/2012 |
| WO | WO-2013/182990 | 12/2013 |
| WO | WO-2014/121342 | 8/2014 |
| WO | WO-2014/125075 | 8/2014 |
| WO | WO-2014/176634 | 11/2014 |
| WO | WO-2014/200705 | 12/2014 |
| WO | WO-2015/071668 | 5/2015 |
| WO | WO-2015/143654 | 10/2015 |
| WO | WO-2016/004166 | 1/2016 |
| WO | WO-2016/038035 | 3/2016 |
| WO | WO-2016/080846 | 5/2016 |
| WO | WO-2016/138286 | 9/2016 |
| WO | WO-2016/144569 | 9/2016 |
| WO | WO-2016/144979 | 9/2016 |
| WO | 2016193136 A1 | 12/2016 |
| WO | WO-2016/210247 | 12/2016 |
| WO | WO-2016/210289 | 12/2016 |
| WO | WO-2017/040864 | 3/2017 |
| WO | WO-2017/157997 | 9/2017 |
| WO | 2018051102 A1 | 3/2018 |
| WO | 2018141063 A1 | 8/2018 |
| WO | WO-2018/173069 | 9/2018 |
| WO | WO-2019/038443 | 2/2019 |
| WO | 2019192968 A1 | 10/2019 |
| WO | 2020039073 A1 | 2/2020 |
| WO | 2020091804 A1 | 5/2020 |
| WO | 2020176067 A1 | 9/2020 |
| WO | 2021076922 A1 | 4/2021 |
| WO | 2021198116 A1 | 10/2021 |

OTHER PUBLICATIONS

Chirife et al., "In vitro antibacterial activity of concentrated polyethylene glycol 400 solutions," Antimicrobial Agents and Chemotherapy, 24(3), pp. 409-412 (1983).

Coburn, "Potential Salicylamide Antiplaque agents: In vitro antibacterial activity against actinomyces viscosus," J. Med. Chem., 24, pp. 1245-1249 (1981).

Cooper et al., "Systematic review of Propionibacterium acnes resistance to systemic antibiotics," Med. J. Aust., 169(5), pp. 259-261 (1998).

Daidone et al., "Salicylanilide and its heterocyclic analogues. A comparative study of their antimicrobial activity," Pharmazie, 45(6), pp. 441-442 (1990) (Abstract only).

Dobie et al., "Fusidic acid resistance in Staphylococcus aureus," Arch. Dis. Child, 89, p. 7477 (2004).

Drago et al., "In vitro selection of resistance in Pseudomonas aeruginosa and Acinetobacter spp. by levofloxacin and ciprofloxacin alone and in combination with [3-lactams and amikacin," Journal of Antimicrobial Chemotherapy, 56(2), pp. 353-359 (2005).

(56) References Cited

OTHER PUBLICATIONS

Fischer, et al., Niclosamide Cream: Recipe against bath Dermatitis, Online article, http://www.pharmazeutische-zeitung.de/index.php?id=1481&no_cache=1&sword_list%5B0%5D=holger&sword_list%5B1%5D=reimann, 2006, 6 pages (Machine Translation).

Ghazi et al., "Antibacterial Effect and Toxicity of Synthesized Salicylanilide Derivatives," Zentralblatt fur Mikrobiologie, 3, pp. 225-232 (1986).

Gooyit et al., "Reprofiled anthelmintics abate hypervirulent stationary-phase Clostridium difficile," Sci. Rep., 6(33642) 8 pages (2016).

Hassanzadeh et al., "Bacterial Resistance to Antibiotics in Acne Vulgaris: An In Vitro Study," Indian Journal of Dermatology, 53(3), pp. 122-124 (2008).

Higaki et al., "Susceptibility of Propionibacterium acnes, *Staphylococcus aureus* and *Staphylococcus epidertnidis* to Kampo Formulations," The Journal of International Medical Research, pp. 318-324 (1997).

Hlasta et al., "Novel inhibitors of bacterial two-component systems with gram positive antibacterial activity: pharmacophore identification based on the screening hit closantel," Bioorganic & Medicinal Chemistry Letters, 8(14, 21), pp. 1923-1928 (1998).

Imperi et al., "New Life for an old drug: the anthelmintic drug niclosamide inhibits Pseudomonas aeruginosa quorum sensing," Antimicrob. Agents Chemother., 557,(2), pp. 996-1005 (2013).

Imramovský et al., "Salicylanilide esters of N-protected amino acids as novel antimicrobial agents," Bioorganic and Medicinal Chemistry Letters, 19(2), pp. 348-351 (2009).

Krátký et al., "New amino acid esters of salicylanilides active against MDR-TB and other microbes," European Journal of Medicinal Chemistry, 45(12), pp. 6106-6113 (2010).

Krátký and Vinsova, "Salicylanilide Ester Prodrugs as Potential Antimicrobial Agents—a Review," Current Pharmaceutical Design, 17, pp. 3494-3505 (2011).

Lau et al., "An FDA-Drug Library Screen for Compounds with Bioactivities Against Meticillin-Resistant *Staphylococcus aureus* (MRSA)," Antibiotics, 4, pp. 424-434 (2015).

Lundberg et al., "Efficacy of topical and systemic antibiotic treatment of meticillin-resistant *Staphylococcus aureus* in a murine superficial skin wound infection model," Int. J Antimicrob. Agents, 42(3), pp. 272-275 (2013).

Macielag et al., "Substituted Salicylanilides as inhibitors of twocomponent regulatory systems in bacteria," J. Med. Chem., 41, pp. 2939-2945 (1998).

Matyk et al., "Heterocyclic isosters of antimycobacterial salicylanilides," Farmaco, 60, pp. 399-408 (2005).

Mollaghan et al., "Antistaphylococcal activity of novel salicylanilide derivatives," Curr. Drug Discov. Technol., 9(1), pp. 39-47 (2012).

Mook et al., "Benzimidazole inhibitors from the Niclosamide chemotype inhibit Wnt/[3-catenin signaling with selectivity over effects on ATP homeostasis," Bioorg Med Chem, 25(6), pp. 1804-1816 (Mar. 15, 2017, e-published Feb. 3, 2017).

Muir et al., "Degradation of Niclosamide (2, 5-Dichloro-4'-nitrosalicylanilide) in sediment and water systems," J. Agricultural and Food Chemistry, 30(6), pp. 1028-1032 (1982).

Nomura et al., "*Staphylococcus aureus* and atopic dermatitis," IRYO, pp. 62-66 (2002).

Osmundsen, "Contact Photoallergy to Tribromsalicylanilide," Br. J. Derm, 81, pp. 429434 (1969).

Pauk et al., "New derivatives of salicylamides: preparation and antimicrobial activity against various bacterial species," Bioorganic & Medicinal Chemistry, 2(21), pp. 6574-6581 (2013).

Pospisil, "Isovitalix-chemically definable enricher of culture media for Neisseria gonorrhoeae," Ceskoslovenska Dermatol., 46(1), pp. 23-25 (1971).

Rajamuthiah et al., Repurposing salicylanilide anthelmintic drugs to combat drug resistant *Staphylococcus aureus*, PLoS ONE 10:e0124595, 19 pages (2015).

Rajamuthiah et al., "Whole Animal Automated Platform for Drug Discovery against Multi-Drug Resistant *Staphylococcus aureus*," PloS One, 9(2):e89189, 11 pages (2014).

Rodriguez-Cavallini et al. "Etiologia bacteriana y susceptibilidad a antibioticos en pacientes con acne," Rev. Biomed., 15, pp. 101-106 (2004).

Rolfe, "Chemical Resistance in livesteock—an overview," 18 pages (1990) www.regional.org.au/au/roc/1990/roc199029.htm.

Sanphui et al., "Pharmaceutical Cocrystals of Niclosamide," Crystal Growth & Design, 12(9), pp. 4588-4599 (2012).

Shah and Mohanraj, "High Levels of fusidic acid-resistant *Staphylococcus aureus* in dermatology patients," British Journal of Dermatology, 148, pp. 1018-1020 (2003).

Singh et al., "Synthesis of 5-chloro-3'-nitro-4'-substituted salicylanilides, a new series of anthelmintic and antimicrobial agents," J. Med. Chem., 20(6), pp. 826-829 (1977).

Steffen et al., "Discovery and structure-activity relationships of modified salicylanilides as cell permeable inhibitors of poly(ADP-ribose) glycohydrolase (PARG)," J. Med Chem., 54(15), pp. 5403-5413 (2011).

Swan et al., "The Pharmacology of Halogenated Salicylanilides and Their Anthelmintic Use in Animals," Review Article-Oorsigartikel, J. S. Afr. Vet. Association, 70(2), pp. 61-70 (1999).

Taborsky et al., "Substituted Salicylanilides with antimicrobial activity," J. Amer. Pharm. As., pp. 503-507 (1959).

Tharmalingham et al., "Repurposing the anthelmintic drug niclosamide to combat Helicobacter pylori," Sci. Rep., 8:3701, pp. 1-12 (2018).

Van Tonder et al., "Preparation and physicochemical properties of niclosamide anhydrate and two monohydrates," Int. J. Pharm., 269(2), pp. 417-432 (2004).

Vinsova et al., "Salicylanilide acetates: synthesis and antibacterial evaluation," Molecules, 12(1), pp. 1-12 (2007).

Vinsova et al., "Salicylanilide diethyl phosphates: Synthesis, antimicrobial activity and cytotoxicity," Bioorg. Med. Chem., 22(2), pp. 728-737 (Jan. 15, 2014, e-published Dec. 12, 2013).

Vinsova et al., "Salicylanilides: still a potential antibacterially active group," 53(6), pp. 294-299 (2004) (English Abstract).

Waisser et al., "Antimycobacterial and Antifungal isosterd of salicylanilides," Arch. Pharm. Med. Chem., 336(6-7), pp. 322-335 (2003).

Waisser et al., "Synthesis and Antimycobacterial activity of salicylanilides substituted in position 5," Chem. Pap., 55(2), pp. 121-129 (2001).

Waisser et al., "The Oriented development of antituberculotics: Salicylanilides," Arch. Pharm. Life Sci., 339, pp. 616-620 (2006).

Wu et al., Antihelminthic niclosamide modulates dendritic cells activation and function; Cellular Immunology, 288, pp. 15-23 (2014).

Wulff et al., "Cream formulations protecting against cercarial dermatitis by Trichobilharzia," Parasitology Research, 101(1), pp. 91-97 (2007).

Zhao, et al., Study on in vitro antimicrobial activity of closantel to *Staphylococcus aureus*, Chinese Journal of Nosocomiology, 22(10), pp. 2019-2021, English Abstract (2012).

Enroth, International Encyclopedia of Public Health, 2nd edition, 3:527-531.

UK Standards for Microbiology Investigations, Identification of Clostridium species, Bacteriology—Identification, (Dec. 1, 2015), 8(4):27 pages.

Ahn et al. (Mar. 16, 2017), "Anti-helminthic Niclosamide Inhibits Ras-driven Oncogenic Transformation Via Activation of GSK-3", Oncotarget, 8(19):31856-31863.

Amieva et al. (Jan. 1, 2008), "Host-Bacterial Interactions in Helicobacter Pylori Infection", Gastroenterology, 134(1):306-323.

Backert et al. (Jul. 15, 2016), "The Role of CagA in the Gastric Biology of Helicobacter pylori", Cancer Research, 76(14):4028-4031.

Burock et al. (2018), "Niclosamide a New Chemotherapy Agent? Pharmacokinetics of the Potential Anticancer Drug in a Patient Cohort of the NIKOLO Trial", Journal of Clinical Oncology, 36(15_suppl):1 page.

Burock et al. (2018), "Phase II Trial to Investigate the Safety and Efficacy of Orally Applied Niclosamide in Patients with Metachronous or Sychronous Metastases of a Colorectal Cancer Progressing after Therapy: The NIKOLO Trial", BMC Cancer, 18(1):7 pages.

(56) References Cited

OTHER PUBLICATIONS

Carvalho et al. (2011), "Nitazoxanide Disrupts Membrane Potential and Intrabacterial pH Homeostasis of Mycobacterium tuberculosis", ACS Medicinal Chemistry Letters, 2(11):849-854.
Celli et al. (Aug. 25, 2009), "Helicobacter pylori Moves Through Mucus by Reducing Mucin Viscoelasticity", Proceedings of the National Academy of Sciences, 106(34): 14321-14326.
Censini et al. (Dec. 1996), "cag, a Pathogenicity Island of Helicobacter pylorus, Encodes Type I-specific and Disease-associated Virulence Factors", Proceedings of the National Academy of Sciences, 93(25):14648-14653.
Chan Francis K. (Oct. 4, 2008), "Proton-pump Inhibitors in Peptic Ulcer Disease", The Lancet, 372(9645):1198-1200.
Cheung Dae Y. (Sep. 2017), "Atrophic Gastritis Increases the Risk of Gastric Cancer in Asymptomatic Population in Korea", Gut and Liver, 11 (5):575-576.
Chey et al. (Feb. 2017), "ACG Clinical Guideline: Treatment of Helicobacter pylori Infection", American Journal of Gastroenterology, 112(2):212-238.
Choi et al. (Mar. 22, 2018), "Helicobacter pylori Therapy for the Prevention of Metachronous Gastric Cancer", The New England Journal of Medicine, 378(12):1085-1095.
Chung et al. (Oct. 24-28, 2015), "Diphenyleneiodonium Chloride and Parthenolide Potential Substance for Novel Anti-Helicobacter Pylori Agents", 23rd United European Gastroenterology Week, 1 page.
Correa Pelayo Md (Jun. 2013), "Gastric Cancer: Overview", Gastroenterology Clinics of North America, 42(2):211-217(8 pages).
Damjanov Ivan (May 2005), "Robbins and Cotran Pathologic Basis of Disease, 7th Edition", Shock, 23(5):482-483.
Deen et al. (May 2013), "The Impact of Autophagic Processes on the Intracellular Fate of Helicobacter pylori", Autophagy, 9(5):639-652.
Devine et al. (Feb. 1970), "Spectra of Susceptibility of Neisseria meningitidis to Antimicrobial Agents In Vitro", Journal of Applied Microbiology, 19(2):329-334.
Dubois et al. (2007), "Helicobacter pylori is Invasive and it may be a Facultative Intracellular Organism", Cellular Microbiology, 9(5):1108-1116.
Eom et al. (Feb. 22, 2011), "Use of Acid-suppressive Drugs and Risk of Pneumonia: A Systematic Review and Meta-analysis", CMAJ, 183(3):310-319.
Fifer et al. (Jun. 2016), "Failure of Dual Antimicrobial Therapy in Treatment of Gonorrhea", New England Journal of Medicine, 374(25):2504-2506.
Galmiche et al. (Nov./Dec. 2010), "Targeting of Helicobacter pylori VacA to Mitochondria", Gut Microbes, 1(6):392-395.
Giannouli et al. (2014), "Use of Larvae of the Wax Moth Galleria Mellonella as an in Vivo Model to Study the Virulence of Helicobacter pylori", BMC Microbiology, 14(228):1-10.
Gisbert et al. (2015), "Helicobacter pylori Second-line Rescue Therapy with Levofloxacin-and Bismuth-containing Quadruple Therapy, after Failure of Standard Triple or Non-bismuth Quadruple Treatments", Alimentary Pharmacology & Therapeutics, 41(8):768-775.
Graham et al. (2010), "Helicobacter pylori Treatment in the Era of Increasing Antibiotic Resistance", Gut, 59(8):1143-1153.
Graham David Y. (2015), "Helicobacter pylori Update: Gastric Cancer, Reliable Therapy, and Possible Benefits", Gastroenterology, 148(4):719-731.
Gu Hy (2008), "The Study on the Mechanisms of Helicobacter Pylori Motility in Gastric Mucosal Colonization", Chinese Journal of Laboratory Medicine, 31:733-736.
Guruge et al. (Mar. 31, 1998), "Epithelial Attachment Alters the Outcome of Helicobacter Pylori Infection", Proceedings of the National Academy of Sciences, 95(7):3925-3930.
Hagymáasi et al. (Jun. 7, 2014), "Helicobacter Pylori Infection: New Pathogenetic and Clinical Aspects", World Journal of Gastroenterology, 20(21):6386-6399.

Hamdoun et al. (Mar. 2017), "Drug Repurposing of the Anthelmintic Niclosamide to Treat Multidrug-Resistant Leukemia", Frontiers in Pharmacology, 8(110):1-11.
Hamilton et al. (2018), "Repurposing of Anthelminthics as Anticancer Drugs", Oncomedicine, 3:1-8.
Hassan et al. (Dec. 1991), "Topical Niclosamide as a Protective Agent Against Schistosome Infection", Journal of the Egyptian Society of Parasitology, 21(3):817-822.
Hessey et al. (1990), "Bacterial Adhesion and Disease Activity in Helicobacter Associated Chronic Gastritis", Gut, 31:134-138.
Huemer et al. (2018), "Impact of Antibiotic Treatment on Immune-checkpoint Blockade Efficacy in Advanced Non-Squamous Non-small Cell Lung Cancer", Oncotarget, 9(23):16512-16520.
Imhann et al. (2016), "Proton Pump Inhibitors Affect the Gut Microbiome", Gut, 65(5):740-748.
Jakobsson et al. (Mar. 2010), "Short-Term Antibiotic Treatment Has Differing Long-Term Impacts on the Human Throat and Gut Microbiome", PLoS One, 5(3):1-12.
Kao et al. (Aug. 20, 2018), "The Antiparasitic Drug Niclosamide Inhibits Dengue Virus Infection by Interfering with Endosomal Acidification Independent of mTOR", PLoS One, 12(8):16 pages.
Kato et al. (2002), "Antibiotic Resistance of Helicobacter Pylori Strains in Japanese Children", Journal of Clinical Microbiology, 40(2):649-653.
Kita et al. (2001), "CYP2C19 Genotype Related Effect of Omeprazole on Intragastric pH and Antimicrobial Stability", Pharmaceutical Research, 18(5):615-621.
Kuipers et al. (Apr. 18, 1996), "Atrophic Gastritis and Helicobacter Pylori Infection in Patients with Reflux Esophagitis Treated with Omeprazole or Fundoplication", The New England Journal of Medicine, 334(16):1018-1122.
Kuipers Ernstj. (2006), "Proton Pump Inhibitors and Helicobacter Pylori Gastritis: Friends or Foes?", Basic & Clinical Pharmacology & Toxicology, 99(3):187-194.
Lau et al. (Jul. 2001), "Provision of Phenotype-Matched Blood Units: no Need for Pre-Transfusion Antibody Screening", Haematologica, 86(7):742-748.
Lee et al. (2014), "Helicobacter pylori CagA Promotes Snail-mediated Epithelial-mesenchymal Transition by Reducing GSK-3 Activity", Nature Communications, 5(4423):1-13.
Malfertheiner et al. (2012), "Management of Helicobacter pylori infectiondthe Maastricht IV/ Florence Consensus Report", Gut, 61:646-664.
Matos et al. (2013), "Helicobacter pylori CagA and VacA Genotypes and Gastric Phenotype: A Meta-analysis", European Journal of Gastroenterology & Hepatology, 25(12):1431-1441.
McGuckin et al. (Oct. 2007), "Muc1 Mucin Limits Both Helicobacter Pylori Colonization of the Murine Gastric Mucosa and Associated Gastritis", Gastroenterology, 133(4):1210-1218.
Mohammad et al. (2018), "Repurposing Niclosamide for Intestinal Decolonization of Vancomycin-resistant Enterococci", International Journal of Antimicrobial Agents, 51(6):897-904.
Nemeth et al. (Feb. 2015), "Bacteriostatic Versus Bactericidal Antibiotics for Patients with Serious Bacterial Infections: Systematic Review and Meta-analysis", The Journal of Antimicrobial Chemotherapy, 70(2):382-395.
Nguyen et al. (Sep. 1999), "Host Determinants of Helicobacter Pylori Infection and its Clinical Outcome", Helicobacter pylori, 4(3):185-197.
Noto et al. (2016), "The Mongolian Gerbil: A Robust Model of Helicobacter pylori-Induced Gastric Inflammation and Cancer", Methods in Molecular Biology, 1422:263-280(20 pages).
Odenbreit Stefan (2005), "Adherence Properties of Helicobacter pylori: Impact on Pathogenesis and Adaptation to the Host", International Journal of Medical Microbiology, 295(5):317-324.
Ottemann et al. (Apr. 2002), "Helicobacter pylori Uses Motility for Initial Colonization and to Attain Robust Infection", Infection and Immunity, 70(4):1984-1990.
Papastergiou et al. (Jan. 14, 2016), "Helicobacter pylori and Colorectal Neoplasia Is there a Causal Link?", World Journal of Gastroenterology, 22(2):649-658.

(56) References Cited

OTHER PUBLICATIONS

Papastergiou et al. (Aug. 7, 2014), "Treatment of Helicobacter Pylori Infection Meeting the Challenge of Antimicrobial Resistance", World Journal of Gastroenterology, 20(29):9898-9911.
Peek Jr. et al. (Jan. 2002), "Helicobacter pylori and Gastrointestinal Tract Adenocarcinomas", Nature Reviews Cancer, 2(1):28-37.
Pereira et al. (Jan. 21, 2014), "Role of Helicobacter pylori in Gastric Mucosa-associated Lymphoid Tissue Lymphomas", World Journal of Gastroenterology, 20(3):684-698.
Romano Md et al. (2004), "Eradication of Helicobacter pylori: A Clinical Update", MedGenMed : Medscape general medicine, 6(1):19.
Schenk et al. (2000), "Effect of Helicobacter Pylori Eradication on Chronic Gastritis During Omeprazole Therapy", Gut, 46:615-621.
Sekirov et al. (Oct. 2008), "Antibiotic-induced Perturbations of the Intestinal Microbiota Alter Host Susceptibility to Enteric Infection", Infection and Immunity, 76(10):4726-4736.
Sherwood et al. (2002), "Impact of Acid Secretion, Gastritis, and Mucus Thickness on Gastric Transfer of Antibiotics in Rats", Gut, 51(4):490-495.
Shimada et al. (Oct. 2007), "Role of Helicobacter Pylori Eradication in the Prevention of Peptic Ulcer in NSAID Users", Nihon Rinsho, 65(10):1824-1829.
Shiota et al. (Sep. 2015), "Antibiotic Resistance of Helicobacter pylori Among Male United States Veterans", Clinical Gastroenterology and Hepatology, 13(9):1616-1624 (17 pages).
Stiefel et al. (Nov. 2006), "Suppression of Gastric Acid Production by Proton Pump Inhibitor Treatment Facilitates Colonization of the Large Intestine by Vancomycin-Resistant *Enterococcus* spp. and *Klebsiella pneumoniae* in Clindamycin-Treated Mice V", Antimicrob Agents Chemother, 50(11): 3905-3907.
Takagi et al. (2018), "The Influence of Long-term Use of Proton Pump Inhibitors on the Gut Microbiota: An Age-sex-matched Case-control Study", Journal of Clinical Biochemistry and Nutrition, 62(1):100-105.
Tam et al. (Dec. 7, 2018), "Host-targeted Niclosamide Inhibits C. Difficile Virulence and Prevents Disease in Mice Without Disrupting the Gut Microbiota", Nature Communications, 9(5233):11 pages.
Thompson et al. (Nov. 1, 2017), "P1.07-008 Microbiome & Immunotherapy Antibiotic Use Is Associated with Inferior Survival for Lung Cancer Patients Receiving PD-1 Inhibitors", Journal of Thoracic Oncology, Abstract Only, 12(11S2): S1998.
Thung et al. (Feb. 2016), "Review Article: The Global Emergence of Helicobacter Pylori Antibiotic Resistance", Alimentary Pharmacology & Therapeutics, 43(4):514-533.
Uemura et al. (Aug. 1997), "Effect of Helicobacter Pylori Eradication on Subsequent Development of Cancer After Endoscopic Resection of Early Gastric Cancer", Cancer Epidemiology, Biomarkers & Prevention, 6(8):639-642.
Unemo Magnus (2015), "Current and Future Antimicrobial Treatment of Gonorrhoea—The Rapidly Evolving Neisseria Gonorrhoeae Continues to Challenge", BMC Infectious Diseases, 15(364):15 pages.
Wu et al. (Jan. 2013), "Diagnostic Accuracy of Narrow-band Imaging for the Differentiation of Neoplastic from Non-neoplastic Colorectal Polyps: a Meta-analysis", Colorectal Dis, 15(1):3-11.
Yamaoka et al. (1997), "Induction of Various Cytokines and Development of Severe Mucosal Inflammation by cagA Gene Positive Helicobacter Pylori Strains", Gut, 41(4):442-451.
Yu et al. (2018), "Niclosamide Exhibits Potent Anticancer Activity and Synergizes with Sorafenib in Human Renal Cell Cancer Cells", Cell Physiol Biochem, 47(3):957-971.
Yutin et al. (Oct. 2013), "A genomic update on clostridial phylogeny: Gram-negativespore-formers and other misplaced Clostridia,", Environ Microbial, 15(10): 2631-2641 (17 pages).
U.S. Appl. No. 17/290,386, filed Apr. 30, 2021.
Gwisai; Biomed. Mater. 2017, 12, 045010. DOI: 10.1088/1748-605X/aa7105 (Year: 2017).
Hu; Front. Cell. Infect. Microbiol., 2017, 7, 168. DOI: 10.3389/fcimb.2017.00168 (Year 2017).
Kadri; ChemMedChem 2018, 13, 1088-1091. DOI:10.1002/cmdc.201800100 (Year: 2018).
Kratky; Bioorg. Med. Chem. 2016, 24, 1322-1330. DOI: 10.1016/j.bmc.2016.02.004 (Year: 2016).
Sun; Tubercle and Lung Disease 1999, 79, 319-320. DOI: 10.1054/tuld.1999.0212 (Year 1999).
Van Doorn; Gut 2000, 46, 321-326. DOI: 10.1136/gut.46.3.321 (Year: 2000).
Zhu; Bioorg. Med. Chem. 2009, 17, 5139-5145. DOI: 10.1016/j.bmc.2009.05.054 (Year 2009).
Jabs et al, "Guidelines for the Use of Immunosuppressive Drugs in Patients with Ocular Inflammatory Disorders: Recommendations of an Expert Panel", American Journal of Ophthalmology, vol. 130, No. 4; pp. 492-513, Oct. 2000.
Ofori-Adjei, et al; "A review of the safety of niclosamide, pyrantel, triclabendazole and oxamniquine" The International Journal of Risk & Safety in Medicine. 2008; 20: pp. 113-122.
Pearson, et al; "Niclosamide Therapy for Tapeworm Infections"; Annals of Internal Medicine. 1985; vol. 102, No. 4; pp. 550-551.

\* cited by examiner

ANTIBACTERIAL USE OF HALOGENATED SALICYLANILIDES

CROSS-REFERENCES TO RELATED APPLICATIONS

This application is a continuation of U.S. patent application Ser. No. 16/125,511, filed Sep. 7, 2018, which is a continuation of U.S. patent application Ser. No. 15/510,304, filed Mar. 10, 2017, which is a U.S. National Phase Application of PCT International Application No. PCT/EP2015/070495, filed Sep. 8, 2015, which is an International Application of and claims the benefit of priority to Swedish Patent Application No. 1451054-9, filed on Sep. 12, 2014, the entire contents of which are herein incorporated by reference.

FIELD OF INVENTION

The invention relates to the halogenated salicylanilides closantel, rafoxanide, oxyclozanide or niclosamide and derivatives thereof including salts, hydrates, esters for use in the topical treatment or prevention of conditions caused by Gram positive bacteria such as Staphylococcus, in particular Staphylococcus aureus, and Streptococcus, in particular Streptococcus pyogenes. The halogenated salicylanilides have a surprisingly low frequency of appearance of resistant mutants in said strains compared to commonly used topical antibiotics. Also provided are topical formulations comprising a halogenated salicylanilide.

BACKGROUND OF THE INVENTION

Today, there are many different classes of antibiotics available to medical practitioners. However, many of the bacteria that these antibiotics are designed to treat are quickly developing resistance to drugs in all classes. Unfortunately the large pharmaceutical companies have limited there research in finding new antibiotics. Several bacteria have become particularly prominent in recent years and have garnered substantial media attention, especially methicillin-resistant Staphylococcus aureus ("MRSA") and Streptococcus pyogenes. MRSA infections on the skin and in the airways are common in hospital settings and the broad spectrum resistance of the bacteria to almost all classes of antibiotics (e.g. methicillin, fusidic acid and mupirocin) make it particularly difficult to combat. MRSA infections in patients who have not recently been in hospital (so called community acquired MRSA infections) are becoming increasingly frequent.

The problem of antibiotic resistance is an increasing problem, but a truly comprehensive solution to the problem has yet to emerge. A major problem in the battle against antibiotic resistance is the lack of novel antibiotics to replace those that no longer effectively treat organisms due to resistance development. New treatments are urgently needed to address this issue of drug resistance.

Fusidic acid is an antibiotic derived from Fusidium coccineum that has been used for over 35 years to treat infections with Staphylococcus aureus. In particular, fusidic acid is prescribed for skin infections caused by Staphylococcus aureus. Such infections include impetigo, angular cheilitis (an infection around the mouth), and infected dermatitis. It works by stopping the growth of the bacteria causing the infection.

Fusidic acid resistance in S. aureus can be readily selected for by in vitro exposure to the antibiotic, leading to the recommendation that for systemic therapy fusidic acid should only be given in combination with another agent. More controversial is the use of topical fusidic acid in the treatment of cutaneous and soft tissue infections.

Increasing fusidic acid resistance in Staphylococcus aureus might be important for three reasons. First, it might mean that systemic fusidic acid can no longer be used in situations where it is clinically indicated. Second, failure of topical treatment may occur, especially in primary care settings where treatment is often empiric. Third, resistance to fusidic acid might be linked to other antibiotic resistances, therefore favoring spread of multiply antibiotic resistant Staphylococcus aureus such as MRSA (methicillin-resistant S. aureus).

Mupirocin is a topical antibiotic used to treat superficial skin infections and to control the spread of methicillin-resistant Staphylococcus aureus (MRSA). Mupirocin resistance was observed shortly after it became available. Prevalence of mupirocin resistance among MRSA isolates has been described mostly in hospitalized adult and elderly patients with wide variability, ranging from 0 to 65% of isolates. Rates of resistance have been shown to correlate with increased use in closed inpatient settings. Very restrictive mupirocin prescriptions for local treatment are now recommended.

Impetigo is a highly contagious bacterial infection of the superficial layers of the epidermis. Impetigo is one of the most common skin diseases among children, accounting for about 10% of skin diseases treated in US paediatric clinics. The bacteria typically considered to be responsible are Staphylococcus aureus and Streptococcus pyogenes, and often a combination of the two. Impetigo is usually transmitted by direct contact but fomites also play an important role. Methicillin-resistant Staphylococcus aureus (MRSA) is being found with increasing frequency as a causative bacteria of impetigo. Impetigo has three common clinical varieties: impetigo contagiosa (common impetigo), bullous impetigo, and ecthyma. Features of all three types of impetigo, however, may coexist in any individual patient.

A number of topical compositions containing pharmaceutically active ingredients are known for the treatment of impetigo. Topical mupirocin 2% (Bactroban ointment and cream) is a treatment option, as are older treatments, such as topical gentian violet and vioform. For many patients, mupirocin is a viable treatment option for MRSA, however, resistance of bacteria to mupirocin has been widely reported.

Topical fusidic acid 2% (Fucidin cream) is used for treatment of impetigo, and is thought to be equally as effective as mupirocin. However, the utility of fusidic acid for treatment of impetigo is limited by the problem of resistance development, as discussed above.

Fusidic acid-resistant Staphylococcus aureus (FRSA) has been identified as a causative bacteria in outbreaks of impetigo and its emergence has been associated with increased use of topical fusidic acid. Accordingly, utility of fusidic acid as first-line agent for the treatment of impetigo is questionable due to current resistance levels in the target bacteria. Retapamulin 1% (Altabax ointment), recently approved by the FDA, is a drug in the new class of pleuromutilin antibiotics for the topical treatment of impetigo due to Staphylococcus aureus (methicillin-susceptible only) or Streptococcus pyogene.

A wound is an injury to the body (as from violence, accident, or surgery) that typically involves laceration or breaking of a membrane (as the skin) and usually damage to underlying tissues (Merriam Webster Dictionary). Burns are injuries to tissues caused by heat, friction, electricity, radiation, or chemicals. Wounds and burns are often colonized by microbiologic pathogens, including Gram-positive bacteria, such as *Staphylococcus aureus* and/or *Streptococcus pyogenes*; and Gram-negative bacteria, e.g. *Pseudomonas aeruginosa*.

Despite the very common occurrence of skin infections, only a limited number of topical antibiotics are approved for the treatment of wounds and particularly infected wounds. Mupirocin (Bactroban) is an antibiotic, developed by GSK. Emerging resistance to mupirocin is becoming a concern. In coagulase-negative staphylococci isolates, mupirocin resistance rates are higher, ranging from 12.7% in Europe to 38.8% in the United States. Retapamulin (Altabax, GSK) is another topical antibiotic used for wound treatment. Fucidin (LEO Pharma) is also effective in primary and secondary skin infections caused by sensitive strains of *Staphylococcus aureus, Streptococcus* species and *Corynebacterium minutissimum*.

Bacterial infections are a leading cause of death worldwide, and bacterial resistance is greatly reducing available treatment options. There is therefore a need for new antibiotics, for which development of resistance is not widespread in the target bacteria, for the prevention and treatment of topical infections caused or contributed to Gram-positive bacteria such as *Staphylococcus aureus* and *Streptococcus pyogenes* is strongly warranted.

The halogenated salicylanilides are a series of compounds generally used as anthelmintic agents. One such compound is niclosamide (5-chloro-N-(2-chloro-4-nitrophenyl)-2-hydroxybenz-amide; also known as 2',5-dichloro-4'-nitrosalicylanilide, 2-hydroxy-5-chloro-N-(2-chloro-4-nitrophenyl)-benzamide, 5-chloro-2'-chloro-4'-nitrosalicylanilide or 5-chloro-N-(2-chloro-4-nitrophenyl)-salicylamide):

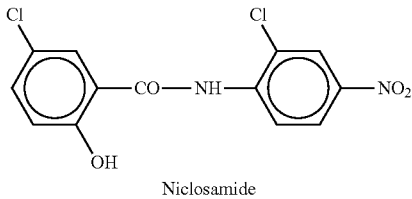

Niclosamide

Acute toxicity of niclosamide:
$LD_{50}$, mice, p.o., >5000 mg/kg
$LD_{50}$, rats, p.o., 5000 mg/kg
$LD_{50}$, rats, dermal, 2000 mg/kg
$LD_{50}$, rabbits, p.o., 5000 mg/kg
$LD_{50}$, cats, p.o., >1000 mg/kg Niclosamide is a known taenicide (=tapeworm killer) effective against several parasitic tapeworms of livestock and pets (e.g. *Taenia* spp, *Moniezia* spp) and also against rumen flukes (*Paramphistomum* spp) and blood flukes (*Schistosoma* spp). This is in contrast with most other salicylanilides, which generally exhibit activity as flukicides but not as taenicides.

Niclosamide is currently used in humans as an anthelmintic drug to treat intestinal infections and displays overall low toxicity, it is poorly soluble in water, shows low intestinal absorption, and once in the bloodstream, it is quickly cleared via the urinary tract or by enzymatic metabolism in the liver. Therapeutically it is useful against cestoda in humans.

Niclosamide has also been shown to prevent the penetration of *Schistosoma mansoni* through the human skin. As well as used as an anticancer drug, pesticide and as an anti-trypanosoma drug. Virtually all applications and proposed applications of niclosamide target eukaryotic organisms.

Niclosamide has also been shown to inhibit viral replication in human cells. However, the mechanism is believed to be through targeting human host cells to provide conditions that prevent the viral life rather than specifically targeting the virus. Accordingly, the viral application of niclosamide result from its ability to target an eukaryotic process.

Niclosamide is commercially available in a number of formulations including, but not limited to Bayer73®, Bayer2353®, Bayer25648®, Bayluscid®, Baylucide®, Cestocid®, Clonitralid, Dichlosale®, Fenasal®, HL 2447®, Iomesan®, Iomezan®, Manosil®, Nasemo®, Niclosamid®, Phenasal®, Tredemine®, Sulqui®, Vermitid®, Vermitin® and Yomesan®.

Other halogenated salicylanilide compounds are Closantel, (N-[5-chloro-4-[(4-chlorophenyl)cyanomethyl]-2-methylphenyl]-2-hydroxy-3,5-diiodobenzamide) is used as a veterinary anthelmintic:

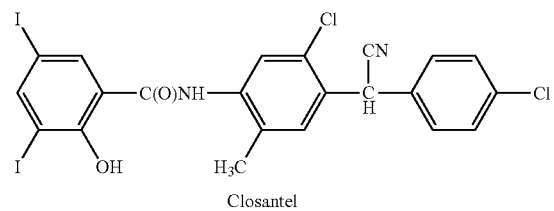

Closantel

Acute toxicity of closantel:
$LD_{50}$, rats, p.o., 262-342 mg/kg (depending on the study), median 302 mg/kg
$LD_{50}$, rats, s.c., 67 mg/kg
$LD_{50}$, mice, p.o., 331 mg/kg
$LD_{50}$, mice, i.m., 57 mg/kg Rafoxanide (3'-chloro-4'-(p-chlorophenoxy)-3,5-diiodosalicylanilide) is known for veterinary use as a fasciolicide and anthelmintic.

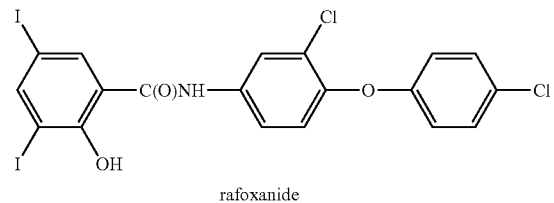

rafoxanide

Acute toxicity of rafoxanide:
$LD_{50}$, rats, p.o., 980->2000 mg/kg (depending on the study), median>1490 mg/kg
$LD_{50}$, mice, p.o., 232-300 mg/kg (depending on the study), median 266 mg/kg
$LD_{50}$, rabbits, p.o., 3200 mg/kg Oxyclozanide (3,3',5,5',6-pentachloro-2'-hydroxysalicylanilide), is known for veterinary use as an anthelmintic, primarily against trematodes.

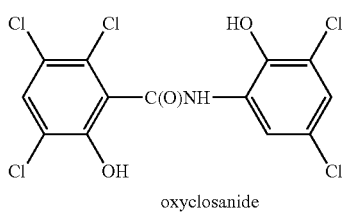

oxyclosanide

LD$_{50}$, rats, p.o., 980-3519 mg/kg (depending on the study), median 2250 mg/kg LD$_{50}$, mice, p.o., 300 mg/kg LD$_{50}$, rabbits, p.o., 3200 mg/kg Low safety margin after oral administration The molecular mode of action of salicylanilides, including niclosamide, is not completely elucidated. They all are uncouplers of the oxidative phosphorylation in the cell mitochondria, which disturbs the production of ATP. This impairs the parasites motility and probably other processes as well. Niclosamide acts on the tapeworms also through inhibition of glucose absorption Niclosamide has been proposed as a possible systemic treatment for chronic lung infections caused by the proteobacterium *Pseudo-monas aeruginosa* and the actinobacterium *Mycoplasmum tuberculosis*. Niclosamide has been shown to reduce the quorum sensing response as well as the production of quorum sensing metabolites in *P. aeruginosa*. Since quorum sensing is considered an important process for the pathogenicity during chronic lung infections caused by this bacterium, it led to proposal that niclosamide could be used as an adjuvant therapy for these infections. Niclosamide does not affect the growth of *P. aeruginosa* and accordingly does not have any direct antibacterial activity. The concentration required for optimal activity was 20 µM, however, some inhibition was detected at 1 µM. (F. Imperi et al., Antimicrobial, Agents and Chemotherapy, 557(2), 996-1005 (2013)).

Ghazi et al. (Zentralbl. Mikrobiol. 141 (1986), 225-232) tested the antibacterial effect and toxicity of synthesized salicylanilide derivatives against *Escherichia coli, Bacillus subtilis, Pseudomonas aeruginosa* and *Staphylococcus aureus* but nothing is mentioned about the rate of resistance development.

J. Vinsova et al. describe the antibacterial activity of salicylanilides (*Molecules*, vol. 12, no. 1, pp. 1-12, 2007; *Bioorganic and Medicinal Chemistry Letters*, vol. 19, no. 2, pp. 348-351, 2009; *European Journal of Medicinal Chemistry*, vol. 45, no. 12, pp. 6106-6113, 2010), but nowhere mentioned the problem with resistance development.

M. J. Macielag et al. tested the antibacterial activity of closantel and related derivatives against the drug-resistant organisms, methicillin-resistant *Staphylococcus aureus* (MRSA) and vancomycin-resistant *Enterococcus faecium* (VREF) (J. Med. Chem., 41(16), 2939-45 (1998)) but nowhere mentioned the problem with resistance development.

D. J. Hlasta et al found that closantel had antibacterial activity against drug resistant *S. aureus* and *E. faecium* (Bioorg. Med. Chem. Letters, 8(14), 1923-28 (1998)), but nowhere mentioned the problem with resistance development.

R. Rajamuthiah et al. identified closantel as a hit in a high throughput liquid screening assay and found anti-staphylococcal activity of closantel against vancomycin-resistant *S. aureus* isolates and other Gram-positive bacteria. There is no mention of the problem of resistance development (PloS One, 2014, 9(2): e89189).

WO 2008/155535 describes the use of halogenated salicylanilides for the treatment of acne, wherein propionibacteria is the bacteria causing the acne. There is no mention of the problem with resistance development.

SUMMARY OF THE INVENTION

Many bacteria are resistant to, or rapidly develop, resistance against antibiotic agents and thus it is undesirable or ineffective to treat a mammal suffering from a topical bacterial disease or infection caused by bacteria that are resistant to the antibiotics. Described herein is the topical use of a halogenated salicylanilide for the treatment of an infection caused by Gram positive bacteria. The topical use of the halogenated salicylanilides according to the invention have a substantially reduced frequency of spontaneous resistant mutants compared to commonly used topical antibiotics.

In a first aspect of the invention there is provided a halogenated salicylanilide selected from the group consisting of closantel, rafoxanide, oxyclozanide and niclosamide and derivatives thereof including salts, hydrates and esters for use in topical prevention or treatment of an infection or disease caused by Gram positive bacteria, wherein the Gram positive bacteria is not a propionibacteria. The invention thus provides a method of treating a disease or infection caused by Gram positive bacteria in a subject, the method comprising topically administering to the subject an effective amount of a halogenated salicylanilide selected from the group consisting of closantel, rafoxanide, oxyclozanide and niclosamide and derivatives thereof including salts, hydrates and esters; wherein the Gram positive bacteria is not a propionibacteria.

In a second aspect of the invention there is provided a halogenated salicylanilide selected from the group consisting of closantel, rafoxanide, oxyclozanide and niclosamide and derivatives thereof including salts, hydrates and esters for use in the topical prevention or treatment of an infection or disease by Gram-positive bacteria which is resistant to a drug selected from fusidic acid, mupirocin and retapamulin. The invention thus provides a method of treating or preventing a disease or infection caused by Gram positive bacteria in a subject, the method comprising topically administering to the subject an effective amount of a halogenated salicylanilide selected from the group consisting of closantel, rafoxanide, oxyclozanide and niclosamide and derivatives thereof including salts, hydrates and esters; wherein the Gram-positive bacteria which is resistant to a drug selected from fusidic acid, mupirocin and retapamulin.

In a third aspect of the invention there is provided a halogenated salicylanilide selected from the group consisting of closantel, rafoxanide, oxyclozanide and niclosamide and derivatives thereof including salts, hydrates and esters for use in topical prevention or treatment of an infection or disease for which fusidic acid, mupirocin or retapamulin was an approved treatment in Europe on 12 Sep. 2014; wherein the disease or infection is caused by Gram positive bacteria. Similarly, the invention may provide A method of treating or preventing a disease or infection caused by Gram positive bacteria in a subject, the method comprising topically administering to the subject an effective amount a halogenated salicylanilide selected from the group consisting of closantel, rafoxanide, oxyclozanide and niclosamide and derivatives thereof including salts, hydrates and esters;

wherein the infection or disease is an infection or disease for which fusidic acid, mupirocin or retapamulin was an approved treatment in the US on 12 Sep. 2014; and wherein the disease or infection is caused by Gram positive bacteria.

The inventors have found that the halogenated salicylanilides closantel, rafoxanide, oxyclozanide, or niclosamide or a pharmaceutically acceptable derivative thereofare highly effective against Gram-positive bacteria, such as *Staphylococcus aureus* and *Streptococcus pyogenes* and unexpectedly are also very effective in reducing the development of resistance bacteria, such as those mentioned above. The compounds are expected to be very useful topical agents for use in the prevention and/or treatment of diseases or infections. One specific halogenated salicylanilide is niclosamide. Examples of diseases which may be treated by topical administration of the halogenated salicylanilide include impetigo, bacterial conjunctivitis, atopic dermatitis related infections, nasal eradication, sycosis barbae, superficial folliculitis, paronychia erythrasma, secondary infected dermatoses, carbuncles, furonculosis (ecthyma, cellulitis, erysipelas, necrotising fasciitis, secondary skin infections of wounds, dermatitis, scabies, diabetic ulcers and the like).

In one embodiment the active ingredient is niclosamide or a derivative thereof or as a hydrate thereof such as niclosamide monohydrate, or salt thereof such as its ethanolamine salt, or piperazine salt or other suitable salts or hydrates of such salts.

Niclosamide is bacteriostatic for *S. aureus* (See FIG. 1), i.e. it prevents the growth, but does not kill the bacterium. Surprisingly, niclosamide has been found to have equally good effect on *S. aureus* strains resistant to methicillin, fusidic acid and mupirocin as non-resistant strains (See FIG. 2). Biological testing (inter alia) has also unexpectedly revealed that the halogenated salicylanilides, and particularly niclosamide have lower mutation rate against MRSA 01 than compounds like fusidic acid, mupirocin and retapamulin (see Table 4).

Without wishing to be bound by a particular theory, it is believed that a number of niclosamide analogs can act in a manner similar to niclosamide. Illustrative niclosamide analogs include, but are not limited to closantel (CAS #: 57808-65-8), oxyclozanide (CAS #: 2277-92-1), rafoxanide (CAS #: 22662-39-1), clioxanide (CAS #: 14437-41-3). Other suitable niclosamide analogs include brotianide (CAS #: 23233-88-7), 4'-chloro-3-nitrosalicylanilide, 4'-chloro-5-nitrosalicylanilide, 2'-chloro-5'-methoxy-3-nitrosalicyl-anilide, 2'-methoxy-3,4'-di-nitrosalicyl-anilide, 2',4'-dimethyl-3-nitrosalicylanilide, $2^1$-chloro-3,4'-dinitrosalicylanilide, 2'-ethyl-3-nitrosalicylanilide, 2'-bromo-3-nitrosalicyl-anilide, and the like (EP2049137). It is noted that these niclosamide analogs are intended to be illustrative and not limiting, Methods of making niclosamide analogs are well known to those of skill in the art (see, e.g. WO 2004/006906), which is herein incorporated by reference for all purposes.

It may be that the halogenated salicylanilide is selected from closantel, rafoxanide, oxyclozanide, niclosamide, clioxanide, brotianide, 4'-chloro-3-nitrosalicylanilide, 4'-chloro-5-nitrosalicylanilide, 2'-chloro-5'-methoxy-3-nitrosalicyl-anilide, 2'-methoxy-3,4'-di-nitrosalicyl-anilide, 2',4'-dimethyl-3-nitrosalicylanilide, 2'-chloro-3,4'-dinitrosalicylanilide, 2'-ethyl-3-nitrosalicylanilide and 2'-bromo-3-nitrosalicyl-anilide, or a pharmaceutically acceptable salt or solvate thereof.

It may be that the halogenated salicylanilide is selected from closantel, rafoxanide, oxyclozanide and niclosamide, or a pharmaceutically acceptable salt or solvate thereof.

It may be that the halogenated salicylanilide is selected from closantel, rafoxanide and oxyclozanide, or a pharmaceutically acceptable salt or solvate thereof.

It may be that the halogenated salicylanilide is niclosamide, or a pharmaceutically acceptable salt or solvate thereof. It may be that the halogenated salicylanilide is niclosamide in the free-base form of the compound. It may be that the halogenated salicylanilide is a pharmaceutically acceptable salt of niclosamide.

In a fourth aspect of the invention there is provided a topical pharmaceutical formulation comprising a halogenated salicylanilide selected from the group consisting of closantel, rafoxanide, oxyclozanide and niclosamide and derivatives thereof including salts, hydrates and esters, wherein the components of the formulation are selected such that it provides a local pH of less than 6 at the site of infection.

The inventors have found that the antibacterial activity of halogenated salicylanilides, e.g. niclosamide, is higher at low pH than at neutral or basic pH. It may be that the formulation does not comprise a buffer or pH modifier. This can mean that the formulation does not significantly alter the naturally low pH of the skin at the site of infection.

It may be that the halogenated salicylanilide, e.g. niclosamide, is in the form of a free base. Halogenated salicylanilides are typically mildly acidic, comprising as they do phenolic groups. Salts of halogenated salicylanilides are typically formed with amines (e.g. ethanolamine) which can provide an increase in local pH.

Bacterial decolonisation may be an effective strategy for reducing the incidence of nosocomial (hospital acquired) infections, particularly those associated with MRSA. Many people carry MRSA without symptoms. Decolonising such patients may be beneficial in the prevention of the spread of MRSA in a hospital environment or to reduce the risk of the patient developing an infection following a surgical or medical procedure in hospital.

In a fifth aspect of the invention there is provided a method of treating, preventing or eliminating bacterial colonization by Gram positive bacteria in a subject, the method comprising topically administering to the subject an effective amount a halogenated salicylanilide selected from the group consisting of closantel, rafoxanide, oxyclozanide and niclosamide and derivatives thereof including salts, hydrates and esters. Thus, the invention may provide a halogenated salicylanilide selected from the group consisting of closantel, rafoxanide, oxyclozanide and niclosamide and derivatives thereof including salts, hydrates and esters, for use in treating, preventing or eliminating bacterial colonization in a subject by Gram positive bacteria by topical administration.

It may be that the halogenated salicylanilide is topically administered to the subject prior to performing a surgical procedure on the subject. It may be that the halogenated salicylanilide is administered to the nose of the subject, either intranasally or to the external skin of the nose. Thus it may be that the halogenated salicylanilide is topically administered to the nose of the subject to performing a surgical procedure on the nose or face of the subject.

It may be that the Gram-positive bacteria develops spontaneous mutations which confer resistance to the halogenated salicylanilide at a frequency of less than $10^{-6}$ at the minimum inhibitory concentration (MIC) of the halogenated salicylanilide to the Gram positive bacteria. It may be that the Gram-positive bacteria develops spontaneous mutations which confer resistance to the halogenated salicylanilide at a frequency of less than $10^{-7}$ at the MIC of the halogenated salicylanilide to the Gram positive bacteria. It may be that the Gram-positive bacteria develops spontaneous mutations which confer resistance to the halogenated salicylanilide at a frequency of less than $10^{-8}$ at the MIC of the halogenated salicylanilide to the Gram positive bacteria. Thus, it may be that the Gram-positive bacteria develops spontaneous mutations which confer resistance to the halogenated salicylanilide at a frequency of less than $4\times10^{-9}$ at the MIC of the halogenated salicylanilide to the Gram positive bacteria.

It may be that the Gram positive bacteria is not a propionibacteria. It may be that the Gram positive bacteria is selected from *Staphylococcus aureus* or *Streptococcus pyogenes*. It may be that the bacteria is resistant to a drug selected from fusidic acid, mupirocin and retapamulin. It may be that the bacteria is methicillin-resistant *Staphylococcus aureus* (MRSA).

It may be that the infection or disease is selected from the group consisting of impetigo, bacterial conjunctivitis, atopic dermatitis and related infections, infected eczema, rosacea, nasal eradication, sycosis barbae, superficial folliculitis, paronychia erythrasma, secondary infected dermatoses, carbuncles, furonculosis, ecthyma, cellulitis, erysipelas, necrotising fasciitis, secondary skin infections of wounds, dermatitis, scabies and diabetic ulcers. Thus it may be that the infection or disease is selected from the group consisting of impetigo, bacterial conjunctivitis and atopic dermatitis. It may be that the infection or disease is selected from the group consisting of impetigo, bacterial conjunctivitis, atopic dermatitis related infections, nasal eradication, sycosis barbae, superficial folliculitis, paronychia erythrasma, secondary infected dermatoses, carbuncles and furonculosis (ecthyma, cellulitis, erysipelas, necrotising fasciitis, secondary skin infections of wounds, dermatitis, scabies, diabetic ulcers and the like).

It may be that the infection or disease is not acne vulgaris.

It may be that the treatment is administered topically for 2 weeks or less.

It may be that the halogenated salicylanilide is comprised in a formulation the components of which are selected such that it provides a local pH of less than 6 at the site of infection. The inventors have found that the antibacterial activity of halogenated salicylanilides, e.g. niclosamide, is higher at low pH than at neutral or basic pH. Thus, it may be that the formulation does not comprise a buffer or pH modifier. Thus, it may be that the halogenated salicylanilide, e.g. niclosamide, is in the form of a free base. The components of the formulation may be selected such that it provides a local pH of greater than 4.5 (e.g. greater than 5) at the site of infection. Reference to a "local pH" is to the pH at the site where the formulation is applied for example the pH on the surface of the skin after applying the formulation containing the halogenated salicylanilide.

It may be that halogenated salicylanilide is selected from rafoxanide, oxyclozanide, closantel and niclosamide and derivatives thereof including salts, hydrates and esters. It may be that halogenated salicylanilide is selected from rafoxanide, oxyclozanide and niclosamide and derivatives thereof including salts, hydrates and esters. Thus, it may be that the halogenated salicylanilide is niclosamide or a salt or hydrate thereof.

It may be that the halogenated salicylanilide (e.g. rafoxanide, oxyclozanide, closantel or niclosamide) is in the form of a free base. It may be that the halogenated salicylanilide (e.g. rafoxanide, oxyclozanide, closantel or niclosamide) is not in the form of a hydrate. Where the halogenated salicylanilide is niclosamide it may be that it is not in the form of the monohydrate.

It may be that the Gram-positive bacteria is not an antibiotic resistant strain. Alternatively, it may be that the Gram-positive bacteria is an antibiotic resistant strain.

It may be that the infection or disease is in a human or animal, for example wherein the infection is in a human.

In some embodiments, the population of Gram-positive bacteria includes antibiotic-resistant Gram-positive bacteria.

It may be that the Gram positive bacteria is not a propionibacteria, e.g. that it is not *Propionibacterium acnes*.

In some embodiments, the population of Gram-positive bacteria includes coccus gram-positive bacteria. In some embodiments, the Gram-positive bacteria are from the *Streptococcus* or *Staphylococcus* genus.

In some embodiments, the Gram-positive bacteria are from the *Streptococcus* genus. It may be that the Gram-positive bacteria are *Streptococcus* selected from *Streptococcus pneumoniae, Streptococcus pyogenes, Streptococcus suis, Streptococcus agalactiae* or *Streptococcus viridans*.

In some embodiments, the Gram-positive bacteria are *Streptococcus pyogenes*

In some embodiments, the Gram-positive bacteria are from the *Staphylococcus* genus. It may be that the Gram-positive bacteria are *Staphylococcus* selected from *Staphylococcus epidermidis, Staphylococcus aureus, Staphylococcus saprophyticus* or *Staphylococcus lugdunensis*. In some embodiments, the coccus Gram-positive bacteria are *Staphylococcus aureus* (e.g. methicillin-resistant *Staphylococcus aureus*).

The Gram-positive bacteria described herein may be resistant to another antibiotic drug. For example, the bacteria may be resistant to another antibiotic drug other than a halogenated salicylanilide selected from closantel, rafoxanide, oxyclozanide and or niclosamide, or a derivative thereof. It may be that the bacteria is resistant to a drug selected from fusidic acid, mupirocin and retapamulin.

Also provided are methods of treating a subject having a Gram-positive bacterial infection that include topically administering to a subject having a Gram-positive bacterial infection one of the halogenated salicylanilides closantel, rafoxanide, oxyclozanide, or niclosamide or a derivative thereof in amounts sufficient to decrease the population of Gram-positive bacteria in the subject. The invention may be and characterized by a rate of developing spontaneous resistance to these bacteria of less than $10^{-6}$, such as less than $10^{-7}$ or $10^{-8}$, such as less than $4\times10^{-9}$. One example which is of special interest is niclosamide.

Furthermore, the present invention provides a method of treating a subject suffering from an infection contributed to or caused by Gram-positive bacteria as hereinbefore described, said method comprising the step of topically administering an effective amount of a halogenated salicylanilide selected from closantel, rafoxanide, oxyclozanide and niclosamide, or a derivative thereof. The invention may be characterized by a rate of developing spontaneous resistance to these bacteria of less than $10^{-6}$, such as less than $10^{-7}$ or $10^{-8}$, such as less than $4\times10^{-9}$. One example which is of special interest is niclosamide which may be characterized by a rate of developing spontaneous resistance to these bacteria of less than $10^{-8}$, such as less than $4\times10^{-9}$.

The present invention may provide the use of a pharmaceutically effective amount of a halogenated salicylanilide selected from closantel, rafoxanide, oxyclozanide and niclosamide or a derivative thereof in the preparation of a medicament for use in the topical prevention and/or treatment of Gram-positive bacteria such as *Staphylococcus aureus* and/or *Streptococcus pyogenes* colonizing or infecting skin affected with a dermatological condition selected from the group consisting of impetigo, atopic dermatitis and infections associated with different skin conditions such as eczema or psoriasis. The invention may be characterized by a rate of developing spontaneous resistance to these bacteria of less than $10^{-6}$, such as less than $10^{-7}$ or $10^{-8}$, such as less than $4 \times 10^{-9}$. One example which is of special interest is niclosamide.

The present invention may provide a method for the topical prevention and/or treatment of Gram-positive bacteria such as *Staphylococcus aureus* and/or *Streptococcus pyogenes* colonizing or infecting skin affected with a dermatological condition selected from the group consisting of impetigo, atopic dermatitis and infections associated with different skin conditions such as eczema or psoriasis comprising administering to a subject a pharmaceutically effective amount of a halogenate salicylanilide selected from closantel, rafoxanide, oxyclozanide and niclosamide or a hydrate or a salt or a hydrate of such a salt thereof. The invention may be characterized by a rate of developing spontaneous mutation frequency less than $10^{-6}$, such as less than $10^{-7}$ or $10^{-9}$, such as less than $4 \times 10^{-9}$. One example which is of special interest is niclosamide.

The present invention may provide a method for the topical treatment of antibiotic-resistant Gram-positive bacterial infections comprising administering to a subject infected with antibiotic-resistant Gram-positive bacteria selected from the group consisting of antibiotic-resistant *Staphylococcus aureus* and/or *Streptococcus pyogenes*, a pharmaceutically effective amount of a halogenated salicylanilide selected from closantel, rafoxanide, oxyclozanide and niclosamide or a hydrate or a salt or a hydrate of such a salt thereof. One example which is of special interest is niclosamide.

The present invention may provide a method for the prevention and/or treatment of conjunctivitis and keratitis caused by Gram-positive bacteria such as *Staphylococcus aureus* and/or *Streptococcus pyogenes* comprising topically administering to a subject a pharmaceutically effective amount of a halogenated salicylanilide selected from closantel, rafoxanide, oxyclozanide and niclosamide or a hydrate or a salt or hydrate of such a salt thereof. One example which is of special interest is niclosamide.

The present invention may provide a pharmaceutical composition comprising a pharmaceutically effective amount of a halogenated salicylanilide selected from closantel, rafoxanide, oxyclozanide and niclosamide or a derivative thereof to be administered for the topical prevention and/or treatment of Gram-positive bacteria such as *Staphylococcus aureus* and/or *Streptococcus pyogenes* colonizing or infecting skin affected with a dermatological condition selected from the group consisting of impetigo, atopic dermatitis and infections associated with different skin conditions such as eczema or psoriasis and characterized by a rate of developing spontaneous resistance to these bacteria of less than $10^{-6}$, such as less than $10^{-7}$ or $10^{-8}$, such as less than $4 \times 10^{-9}$. One example which is of special interest is niclosamide.

The present invention may provide a pharmaceutical composition comprising a pharmaceutically effective amount of niclosamide or a derivative thereof to be administered for the topical prevention and/or treatment of Gram-positive bacteria such as *Staphylococcus aureus* and/or *Streptococcus pyogenes* colonizing or infecting skin affected with a dermatological condition selected from the group consisting of impetigo, atopic dermatitis and infections associated with different skin conditions such as eczema or psoriasis and characterized by a rate of developing spontaneous mutation frequency less than $10^{-6}$, such as less than $10^{-7}$ or $10^{-8}$, such as less than $4 \times 10^{-9}$.

The present invention may provide a pharmaceutical composition comprising niclosamide as the active ingredient to be administered for the topical prevention and/or treatment of Gram-positive bacteria such as *Staphylococcus aureus* and/or *Streptococcus pyogenes* colonizing or infecting skin affected with a dermatological condition selected from the group consisting of impetigo, atopic dermatitis and infections associated with different skin conditions such as eczema or psoriasis and characterized by a rate of developing spontaneous mutation frequency less than $10^{-6}$, such as less than $10^{-7}$ or $10^{-8}$, such as less than $4 \times 10^{-9}$.

Examples of diseases which may be topically treated using the halogenated salicylanilide include impetigo, bacterial conjunctivitis, atopic dermatitis related infections, nasal eradication, sycosis barbae, superficial folliculitis, paronychia erythrasma, secondary infected dermatoses, carbuncles, furonculosis (ecthyma, cellulitis, erysipelas, necrotising fasciitis, secondary skin infections of wounds, dermatitis, scabies, diabetic ulcers and the like).

The infection or disease treated topically using the halogenated salicylanilide may be a skin infection, infected dermatitis or infected dermatosis, for example any of the skin infections described herein. The skin infection may, for example, be selected from impetigo (including impetigo contagiosa, bullous impetigo, and ecthyma) infected dermatitis (for example infected atopic dermatitis) infected eczema, infected skin wounds, infected burns and infected ulcers (for example diabetic ulcers).

The infection or disease treated topically using the halogenated salicylanilide may be a secondarily Gram positive infected dermatosis, for example a secondary skin infection. Secondary Gram positive infections are common complications of primary dermatoses, primary nonbacterial skin infections, traumatic lesions, ulcers, cutaneous infestations, and other skin diseases. Accordingly, the halogenated salicylanilide may be for use in the topical treatment of for example secondary infections of a condition selected from eczema, pediculosis, scabies, insect bites (for example papular urticaria), pemphigus psoriasis, skin ulcers, kerion and a viral infection of the skin (for example herpes simplex or chicken pox).

The halogenated salicylanilide may be for use to decolonise a subject carrying a Gram positive bacteria (including any of the Gram positive bacteria described herein, for example MRSA), wherein the halogenated salicylanilide is applied topically to the subject. Such decolonisation may be effective in preventing or reducing the spread of infection to other subjects particularly in a hospital environment. Decolonisation may also prevent or reduce the risk of surgical site infections resulting from surgical or medical procedures carried out on the patient or at the site of medical devices such as catheters or IV lines or cannula. Accordingly the halogenated salicylanilide may be for use in the decolonisation of a subject prior to carrying out a surgical procedure on the subject, wherein the halogenated salicylanilide is applied topically to the subject. Such surgical procedures include, for example elective surgical procedures such as hip or knee replacement. Decolonisation may be achieved by topically administering the halogenated salicylanilide to sites on the subject which are colonised by the Gram positive bacteria. It is known that a common site for bacterial colonisation such as MRSA is the nose. Accordingly, the halogenated salicylanilide may be applied topically to the nose. Particularly the halogenated salicylanilide may be applied to the anterior nares (the inner surface of the nostrils).

The infections and decolonisation described in the above paragraphs and herein may be topically treated with any of the halogenated salicylanilides herein selected from closantel, rafoxanide, oxyclozanide or niclosamide or a derivative thereof. Particularly the halogenated salicylanilide may be niclosamide.

The present invention may provide a pharmaceutical composition comprising a pharmaceutically effective amount of one of the halogenated salicylanilides closantel, rafoxanide, oxyclozanideor niclosamide or a derivative thereof to be administered for the topical prevention and/or treatment of Gram-positive bacteria such as *Staphylococcus aureus* and/or *Streptococcus pyogenes* colonizing or infecting skin affected with a dermatological condition selected from the group consisting of impetigo, atopic dermatitis and infections associated with different skin conditions such as eczema or psoriasis characterized by a rate of developing spontaneous mutation frequency less than $10^{-6}$, such as less than $10^{-7}$ or $10^{-8}$, such as less than $4 \times 10^{-9}$ against MRSA 01, MRSA 15 and MRSA 16 at a concentration of MIC×1 when measured according to mutational frequency evaluation method as described in the experimental section. Niclosamide has been found to be superior against *S. aureus* and *S. pyogenes* (both in μM and μg/ml).

A further aspect of the invention also provides a halogenated salicylanilide selected from the group consisting of closantel, rafoxanide, oxyclozanide, and niclosamide and derivatives thereof including salts, hydrates and esters for use in the topical prevention or treatment of an infection caused by Gram-positive bacteria, are highly effective in inhibiting the growth of Gram-positive bacteria such as *Staphylococcus*, in particular *Staphylococcus aureus*, and *Streptococcus*, in particular *Streptococcus pyogenes* characterized by a rate of developing spontaneous mutation frequency less than $10^{-6}$, such as less than $10^{-7}$ or $10^{-8}$, such as less than $4 \times 10^{-9}$. One example which is of special interest is niclosamide.

A further aspect of the invention also provides a method for manufacturing of a medicament for use in topical prevention or treatment of an infection caused by Gram-positive bacteria, wherein the medicament is niclosamide and derivatives thereof including salts, hydrates and esters and wherein the use of the halogenated salicylanilide are highly effective in inhibiting the growth of Gram-positive bacteria such as *Staphylococcus*, in particular *Staphylococcus aureus*, and *Streptococcus*, in particular *Streptococcus pyogenes* characterized by a rate of developing spontaneous imitation frequency less than $10^{-6}$, such as less than $10^{-7}$ or $10^{-8}$, such as less than $4 \times 10^{-9}$.

By the topical use of the halogenated salicylanilides, such as niclosamide it is possible to treat a human suffering from an infection caused by bacteria such as *Staphylococcus aureus* or *Streptococcus pyogenes* while having a reduced rate of appearance of spontaneous resistant mutants against the agent.

Further advantages and objects with the present invention will be described in more detail, inter alia with reference to the accompanying drawings.

BRIEF DESCRIPTION OF THE DRAWINGS AND TABLES

FIG. 1 shows microbiological data of niclosamide tested against MRSA, MSSA and *S. pyogenes* strains. A. MIC (μg/ml) against all targeted strains. The MIC of niclosamide was ≤0.4 μg/ml against *S. aureus* strains, including the strains resistant to fusidic acid (*) and the ones resistant to mupirocin (‡), and ≤3.2 μg/ml against *Streptococcus pyogenes* strains. Dose-response curves of yellow highlighted strains are represented in B.

Figure 5:
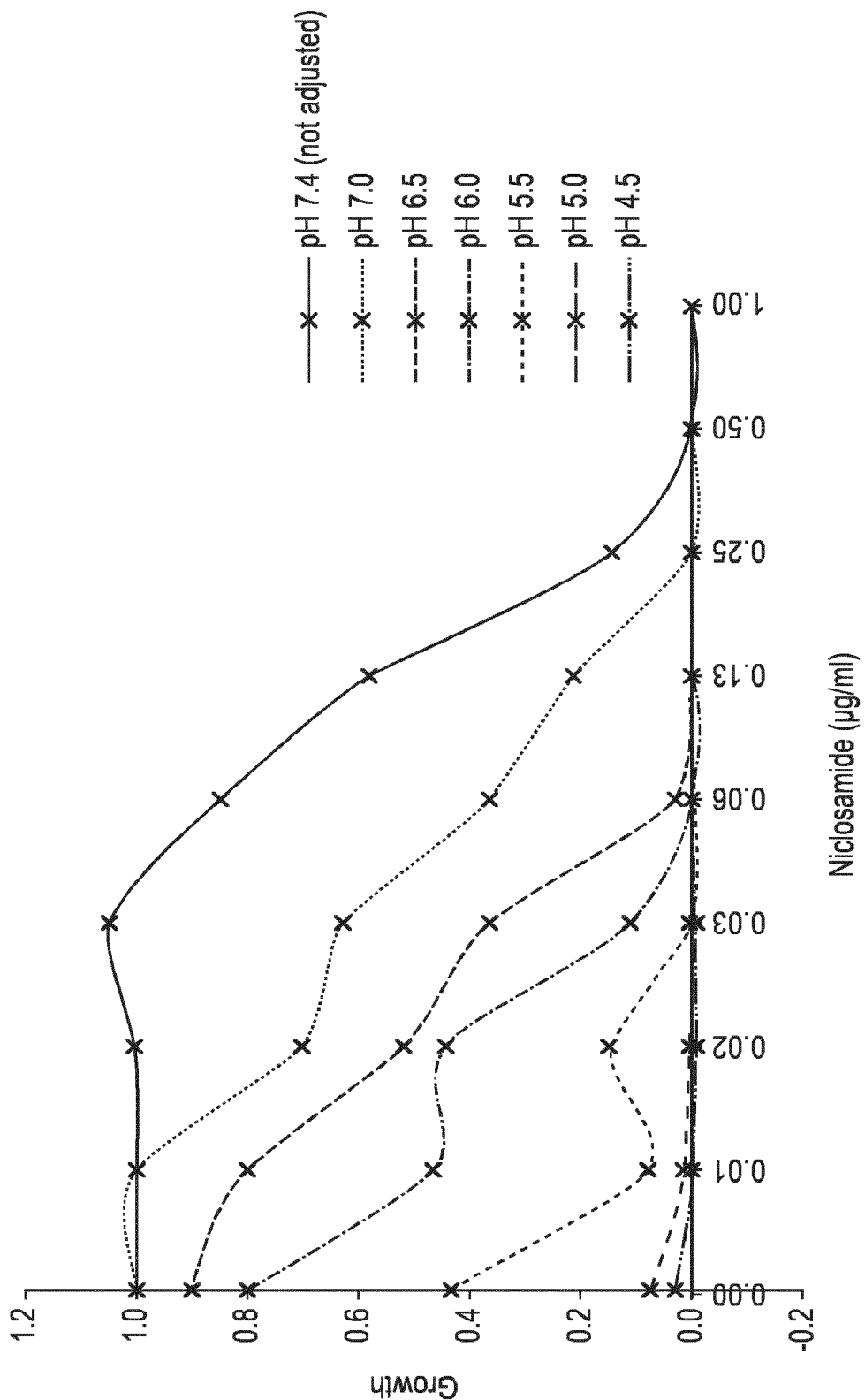

FIG. 5 shows the growth of *S. aureus* at different pH as a function of niclosamide concentration (average of 3 replicates). The growth of *S. aureus* without niclosamide (0 μg/ml) is comparable from pH 7.4 to pH 6.0. The growth without niclosamide is slightly inhibited at pH 5.5 and completely inhibited with pH equal or below 5.0.

DETAILED DESCRIPTION OF THE INVENTION

Definitions

In the context of the present application and invention, the following definitions apply:

The term "*Staphylococcus aureus*" or "*S. aureus*" as used herein, without further description, relates to any strain of the gram-positive bacteria classified as *Staphylococcus aureus*, and which have been associated with a number of infections, including pneumonia, osteomyelitis, arthritis, endocarditis, sepsis and toxic shock syndrome, as well as cause less severe infections of the skin and soft tissues.

The term "methicillin-resistant *Staphylococcus aureus*" or "MRSA" as used herein includes strains of *Staphylococcus aureus* that are resistant to methicillin and can also broadly relate to Gram-positive bacteria strains (e.g. beta-lactamase-producing bacteria) that are resistant to antibiotics falling within the general classification of penicillins. Methicillin is the common name for (2S,5R,6R)-6-[(2,6-dimethoxybenzoyl)amino]-3,3-dimethyl-7-oxo-4-thia-1-azabi-cyclo[3.2.0]heptane-2-carboxylic acid, which is a narrow spectrum beta-lactam antibiotic that has been used to treat infections caused by susceptible Gram-positive bacteria (e.g. including *Staphylococcus aureus*).

The term "derivative" refer to, but shall not be limited to metabolites, pro-drugs (converted into active drugs), esters, hydrates and/or a pharmaceutically acceptable salt and/or hydrates of such salts of the halogenated salicylanilides of the present invention. Also within the term "derivatives" are crystalline forms of the compounds and co-crystals formed between the halogenated salicylanilide and a suitable co-former(s). A person skilled in the art is well aware of various chemical methods and techniques to render a chemical substance to generate a derivate, which still comprises the chemical basis, such as addition, deletion or substitution of a group or functional group and thus it would be easy to generate a similar compound as niclosamide which has the same effect as the original.

The term "pharmaceutically acceptable salt" refers to salts (e.g. ethanolamine or piperazine salts) that retain the biological effectiveness and properties of the compounds described herein and, which are not biologically or otherwise undesirable. Pharmaceutically acceptable salts are well known to skilled persons in the art. Accordingly, it may be that a reference to a salt of a halogenated salicylanilide herein may refer to a pharmaceutically acceptable salt of the halogenated salicylanilide.

The term "solvate" is used herein to refer to a complex of solute, such as a compound or salt of the compound, and a solvent. If the solvent is water, the solvate may be termed a hydrate, for example a monohydrate, dihydrate, trihydrate etc., depending on the number of water molecules present per molecule of substrate.

The term 'treatment' herein indicates (i) the prevention of the disease caused by bacteria, such as *Staphylococcus aureus* and/or *Streptococcus pyogenes*; (ii) the suppression of the disease caused by bacteria, such as *Staphylococcus aureus* and/or *Streptococcus pyogenes*; and (iii) the relief of the disease caused by bacteria, such as *Staphylococcus aureus* and/or *Streptococcus pyogenes*; v) the eradication of a non-symptomatic colonization by *Staphylococcus aureus* from an area on the body, (v) the eradication of Gram-positive bacteria such as *Staphylococcus aureus* and/or *Streptococcus pyogenes* symptomatic infection, (vi) the eradication of Gram-positive bacteria such as *Staphylococcus aureus* and/or *Streptococcus pyogenes*; from an area of the body affected by another disease that could enable establishment of an infection more readily, than in a non-disease affected area—e.g. an area of the skin affected by eczema or atopic dermatitis, (vii) the suppression of the disease caused by Gram-positive bacteria such as *Staphylococcus aureus* and/or *Streptococcus pyogenes*; from an area of the body affected by another non-infectious disease that enables establishment of an infection more readily, than in a non-disease affected area—e.g. an area of the skin affected by eczema or atopic dermatitis.

Thus, in the context of the present invention, treatment of a condition encompasses both therapeutic and prophylactic treatment, of either an infectious or a non-infectious condition, in a mammal such as a human or animal, but in particular a human. It may involve complete or partial eradication of the condition, removal or amelioration of associated symptoms, arresting subsequent development of the condition, and/or prevention of, or reduction of risk of, subsequent occurrence of the condition. The bacterial strain may be characterized by a rate of developing spontaneous mutation frequency less than $10^{-6}$, such as less than $10^{-7}$ or 10', such as less than $4\times10^{-9}$. The treatment will typically involve the use of the halogenated salicylanilides closantel, rafoxanide, oxyclozanide or niclosamide or derivatives thereof against Gram-positive bacteria such as *Staphylococcus aureus* and *Streptococcus pyogenes*. One example which is of special interest is niclosamide.

It may be that the infection or disease which is to be treated is in an animal, e.g. a mammal. In particular, the halogenated salicylanilide can be used to treat commercial animals such as livestock (e.g. cows, sheep, chickens, pigs, geese, ducks, goats, etc.). Alternatively, the compounds of the present invention can be used to treat companion animals such as cats, dogs, horses, etc.

A "topical medication" is a medication that is applied to body surfaces such as the skin or mucous membranes to treat ailments via a large range of classes including but not limited to creams, foams, gels, droplets, lotions, and ointments. Topical medications differ from many other types of drugs because mishandling them can lead to certain complications in a patient or administrator of the drug. Many topical medications are epicutaneous, meaning that they are applied directly to the skin. Topical medications may also be inhalational, such as asthma medications, or applied to the surface of tissues other than the skin, such as eye drops applied to the conjunctiva, or ear drops placed in the ear, or medications applied to the surface of a tooth.

In topical application, a suitable pharmaceutical composition, for example a cream, lotion, gel, ointment, paste, drops or the like, may be spread on the affected surface and gently rubbed in. A solution may be applied in the same way, but more typically will be applied with a dropper, swab, or the like, and carefully applied to the affected areas.

Topical application of the halogenated salicylanilide according to the present invention enables the halogenated salicylanilide to be delivered selectively to a specific site, and avoids inter- and intra-patient variations which may be associated with alternative routes of drug administration.

Topical pharmaceutical compositions according to the present invention may be used to treat a variety of skin or membrane disorders, such as infections of the skin or membranes (e.g. infections of nasal membranes, axilla, groin, perineum, rectum, dermatitic skin, skin ulcers, and sites of insertion of medical equipment such as i.v. needles, catheters and tracheostomy or feeding tubes) with any of the bacteria described above, (e.g. any of the *Staphylococci, Streptococci* such as *S. aureus* (e.g. methicillin resistant *S. aureus* (MRSA)). Particular bacterial conditions that may be treated by topical pharmaceutical compositions of the present invention also include the skin- and membrane-related conditions disclosed hereinbefore, as well as: rosacea (including erythematotelangiectatic rosacea, papulopustular rosacea, phymatous rosacea and ocular rosacea); erysipelas; erythrasma; ecthyma; ecthyma gangrenosum; impetigo; paronychia; cellulitis; folliculitis (including hot tub folliculitis); furunculosis; carbunculosis; staphylococcal scalded skin syndrome; surgical scarlet fever; streptococcal perianal disease; streptococcal toxic shock syndrome; pitted keratolysis; trichomycosis axillaris; pyoderma; external canal ear infections; green nail syndrome; spirochetes; necrotizing fasciitis; Mycobacterial skin infections (such as lupus vulgaris, scrofuloderma, warty tuberculosis, tuberculides, erythema nodosum, erythema induratum, cutaneous manifestations of tuberculoid leprosy or lepromatous leprosy, erythema nodosum leprosum, cutaneous *M. kansasii, M. malmoense, M. szulgai, M. simiae, M. gordonae, M. haemophilum, M. avium, M. intracellular, M. chelonae* (including *M. abscessus*) or *M. fortuitum* infections, swimming pool (or fish tank) granuloma, lymphadenitis and Buruli ulcer (Bairnsdale ulcer, Searles' ulcer, Kakerifu ulcer or Toro ulcer)); as well as infected eczema, burns, abrasions and skin wounds. Particular fungal conditions that may be treated by topical pharmaceutical compositions of the present invention also include the skin- and membrane-related conditions disclosed hereinbefore, as well as: candidiasis; sporotrichosis; ringworm (e.g. tinea pedis, tinea cruris, tinea capitis, tinea unguium or tinea corporis); tinea versicolor; and infections with *Trichophyton, Microsporum, Epidermophyton* or *Pityrosporum ovale* fungi.

In some embodiments of the invention the topical pharmaceutical compositions of the present invention is not used to treat a fungal infection, for example the composition is not used to treat candidiasis; sporotrichosis; ringworm (e.g. tinea pedis, tinea cruris, tinea capitis, tinea unguium or tinea corporis); tinea versicolor; and infections with *Trichophyton*, *Microsporum*, *Epidermophyton* or *Pityrosporum ovale* fungi.

The application regimen will depend on a number of factors that may readily be determined, such as the severity of the condition and its responsiveness to initial treatment, but will normally involve one or more applications per day on an ongoing basis. The effective dosage of the pharmaceutical composition of the present invention varies from the formulation, administration pathway, age, weight and gender of animal or human with a disease caused by *Staphylococcus aureus*, severity of a disease, diet, administration frequency and pathway, excretion and sensitivity.

Generally, the amount of the halogenated salicylanilide or a derivative thereof to be administered topically is in the range of 0.01-10000 mg/cm$^2$, preferably between 0,1-1000 mg/cm$^2$ and even more preferably between 1-100 mg/cm$^2$ using a pharmaceutical formulation containing between 1-20%, preferably 2-10%, more preferably 3-8% and even more preferably 4-6% of active ingredient (all numbers given by weight).

In microbiology, minimum inhibitory concentration (MIC) is the lowest concentration of an antibacterial that will inhibit the visible growth of a microorganism after overnight incubation. Minimum inhibitory concentrations are important in diagnostic laboratories to confirm resistance of microorganisms to an antimicrobial agent and also to monitor the activity of new antimicrobial agents. A MIC is generally regarded as the most basic laboratory measurement of the activity of an antimicrobial agent against an organism.

In toxicology, the median lethal dose, LD$_{50}$ (abbreviation for "lethal dose, 50%") of a toxin, radiation, or pathogen is the dose required to kill half the members of a tested population after a specified test duration. LD$_{50}$ figures are frequently used as a general indicator of a substance's acute toxicity.

Therapeutic index (therapeutic ratio) is defined as the amount of a therapeutic agent causing the therapeutic effect measured as MIC to the amount that causes death in animal studies measured as LD$_{50}$. Some antibiotics require monitoring to balance efficacy with minimizing adverse effects, including: gentamicin, vancomycin, amphotericin B (nicknamed 'ampho-terrible' for this very reason), and polymyxin B. Other MIC values could be used as well.

The rate of resistance development is quantified as the frequency of spontaneous mutants in a population of bacteria that is able to resist a given concentration of the antibiotic. For example the rate of resistance development may by $10^{-9}$ if on average 1 cell in $10^9$ cells is able to survive a concentration of antibiotic corresponding to 1× MIC.

In microbiology, colony-forming unit (CFU) is a rough estimate of the number of viable bacteria or fungal cells in a sample. Viable is defined as the ability to multiply via binary fission under the controlled conditions.

Also disclosed are the following numbered clauses
1. Halogenated salicylanilides selected from the group consisting of closantel, rafoxanide, oxyclozanide and niclosamide and derivatives thereof including salts, hydrates and esters for use in topical prevention or treatment of an infection or disease caused by Gram-positive bacteria, characterized by a rate of developing spontaneous mutation frequency less than $10^{-6}$.
2. The halogenated salicylanilides according to clause 1, characterized by a rate of developing spontaneous mutation frequency less than $10^{-7}$ or $10^{-8}$.
3. The halogenated salicylanilides according to clause 2, characterized by a rate of developing spontaneous mutation frequency less than $4\times10^{-9}$.
4. The halogenated salicylanilides according to any of clauses 1-3, selected from the group consisting of closantel, rafoxanide, oxyclozanide and niclosamide and salts thereof for use in topical prevention or treatment of an infection or disease caused by Gram-positive bacteria, characterized by a rate of developing spontaneous mutation frequency less than $10^{-6}$ or less than $10^{-7}$ or $10^{-8}$ or less than $4\times10^9$.
5. The halogenated salicylanilides according to any of clauses 1-4, selected from the group consisting of closantel, rafoxanide, oxyclozanide and niclosamide for use in topical prevention or treatment of an infection or disease caused by Gram-positive bacteria, characterized by a rate of developing spontaneous Imitation frequency less than $10^{-6}$ or less than $10^{-7}$ or $10^{-8}$ or less than $4\times10^{-9}$.
6. The halogenated salicylanilides according to any of clauses 1-5, wherein the halogenated salicylanilides is niclosamide and derivatives thereof including salts, hydrates and esters for use in topical prevention or treatment of an infection or disease caused by Gram-positive bacteria, characterized by a rate of developing spontaneous mutation frequency less than $10^{-6}$ or less than $10^{-7}$ or $10^{-8}$ or less than $4\times10^{-9}$.
7. The halogenated salicylanilides according to any of clauses 1-6, wherein the halogenated salicylanilides is niclosamide and hydrates of salts thereof or hydrates of such salts for use in topical prevention or treatment of an infection or disease caused by Gram-positive bacteria, characterized by a rate of developing spontaneous mutation frequency less than $10^{-8}$ or less than $4\times10^{-9}$.
8. The halogenated salicylanilides according to any of clauses 1-7, wherein the infection or disease is selected from the group consisting of impetigo, bacterial conjunctivitis, atopic dermatitis and related infections, nasal eradication, sycosis barbae, superficial folliculitis, paronychia erythrasma, secondary infected dermatoses, carbuncles, furonculosis, ecthyma, cellulitis, erysipelas, necrotising fasciitis, secondary skin infections of wounds, dermatitis, scabies and diabetic ulcers.
9. The halogenated salicylanilides according to clauses 8, wherein the infection or disease is selected from the group consisting of impetigo, bacterial conjunctivitis, atopic dermatitis and infections associated with different skin conditions.
10. The halogenated salicylanilides according to any of clauses 1-9, wherein the bacteria is *Staphylococcus aureus* or *Streptococcus pyogenes*.
11. A method for manufacturing a medicament for use in topical prevention or treatment of an infection caused by bacteria, wherein the medicament is niclosamide and derivatives thereof including salts, hydrates and esters and characterized by a rate of developing spontaneous mutation frequency less than $10^{-6}$ or less than $10^{-7}$ or $10^{-8}$ or less than $4\times10^{-9}$.
12. The method for manufacturing a medicament according to clause 11 for use in topical prevention or treatment of an infection caused by bacteria, wherein the medicament is niclosamide and hydrates of salts thereof or hydrates of such salts and characterized by a rate of developing spontaneous mutation frequency less than $10^{-8}$ or less than $4\times10^{-9}$.
13. A pharmaceutical composition comprising niclosamide and derivatives thereof including salts, hydrates, esters and hydrates of such salts as the active ingredient wherein the pharmaceutical composition reduces or eliminates resistance development by the bacteria, *Staphylococcus aureus* or *Streptococcus pyogenes* against the used niclosamide by a rate of developing spontaneous mutation frequency less than $10^{-8}$ or less than $4\times10^{-9}$.

Following examples are intended to illustrate, but not to limit, the invention in any manner, shape, or form, either explicitly or implicitly.

EXAMPLES

Example 1

Experimental tests were conducted to determine the antibacterial activity and the mutation rate conferring resistance for halogenated salicylanilides and reference compounds.

Microorganisms

Chosen for its relevance regarding bacterial skin infections, the methicillin-resistant *S. aureus* (MRSA) 01 strain was used as the primary test microorganism. This strain is a community-acquired MRSA clinical isolate of USA 300 type, from a skin abscess.

Twenty-one other MRSA and methicillin-sensitive *S. aureus* strains, and 4 *Streptococcus pyogenes* strains, were also included in the study (Table 1). These covered fusidic acid- and mupirocin-resistant strains, these two types of resistance being of clinical relevance.

Strains were conserved in Luria Bertani (LB) Broth (*S. aureus*) or Brain Heart Infusion (BHI) (*S. pyogenes*) supplemented with glycerol 15% (v/v) at −80° C., and reactivated by isolation on LB (*S. aureus*) or BHI (*S. pyogenes*) agar plates. Strains were cultivated in Mueller Hinton (MH) Broth-cation adjusted (*S. aureus*) supplemented with lysed horse blood 2.5% (v/v) (*S. pyogenes*). All strains were cultivated at 37° C., aerobically for *S. aureus* strains.

TABLE 1

Strains list and information

| Species | Strains | Mupirocin and fusidic acid Resistance gene | USA type | MLSTSCC mec | spa type | Origin |
|---|---|---|---|---|---|---|
| *S. aureus* | Newman | | | | | |
| | MRSA 01 | | USA 300 | ST8 - IV | t008 | SSI |
| | MRSA 02 | | | ST30-IV | t019 | SSI |
| | MRSA 03 * | ND | USA 400 | ST1-IV | t127 | SSI |
| | MRSA 04 | | | ST772-V | t657 | SSI |
| | MRSA 05 | | | ST130-XI | t843 | SSI |
| | MRSA 06 | | | CC97 - 5C2 (V) | | SSI |
| | MRSA 07 | | | ST398 | | KU |
| | MRSA 08 ‡ | ND | USA 300 | ST8 | | KU |
| | MRSA 09 | | USA600 | ST45 | | KU |
| | MRSA 10 | | | ST22 - IV | | KU |
| | MRSA 11 | | | ST36 - II | | KU |
| | EEFIC 01 * | | | CC123 | t171 | SSI |
| | EEFIC 02 * | | | CC123 | t171 | SSI |
| | MRSA 12 * | fusB | | CC80 | t044 | SSI |
| | MRSA 13 * | fusB | | CC80 | t044 | SSI |
| | MSSA 01 * | fusC | | CC1 | t127 | SSI |
| | MSSA 02 * | fusC | | CC1 | t127 | SSI |
| | MRSA 14 * | fusA | | CC22 | t2006 | SSI |
| | MRSA 15 * | fusA | | CC30 | t166 | SSI |
| | MRSA 16 ‡ | mupA | | CC30 | t019 | SSI |
| | MRSA 17 ‡ | mupB | | CC509 | t375 | SSI |
| *S. pyogenes* | 01 | | | | | SSI |
| | CCUG 25571 | | | | | |
| | ATCC 19615 | | | | | |
| | ATCC 12385 | | | | | |

All *Staphylococcus aureus* strains but one (MRSA 07) are human clinical isolates; MRSA 07 is a Livestock-associated MRSA; MRSA 02 and MRS 04 are Community-associated MRSA;

* strains resistant to fusidic acid;

‡ strains resistant to mupirocin;

ND: Not determined;

EEFIC: Epidemic European Fusidic acid-resistant Impetigo Clone;

MLST: Multilocus Sequence Typing;

SSCmec: staphylococcal cassette chromosome mec;

spa: *S. aureus* protein A;

KU: Copenhagen University;

SSI: National Reference Laboratory for Staphylococci, Statens Serum Instityt, Copenhagen, Denmark.

Antibacterial Activity

Figure 1:
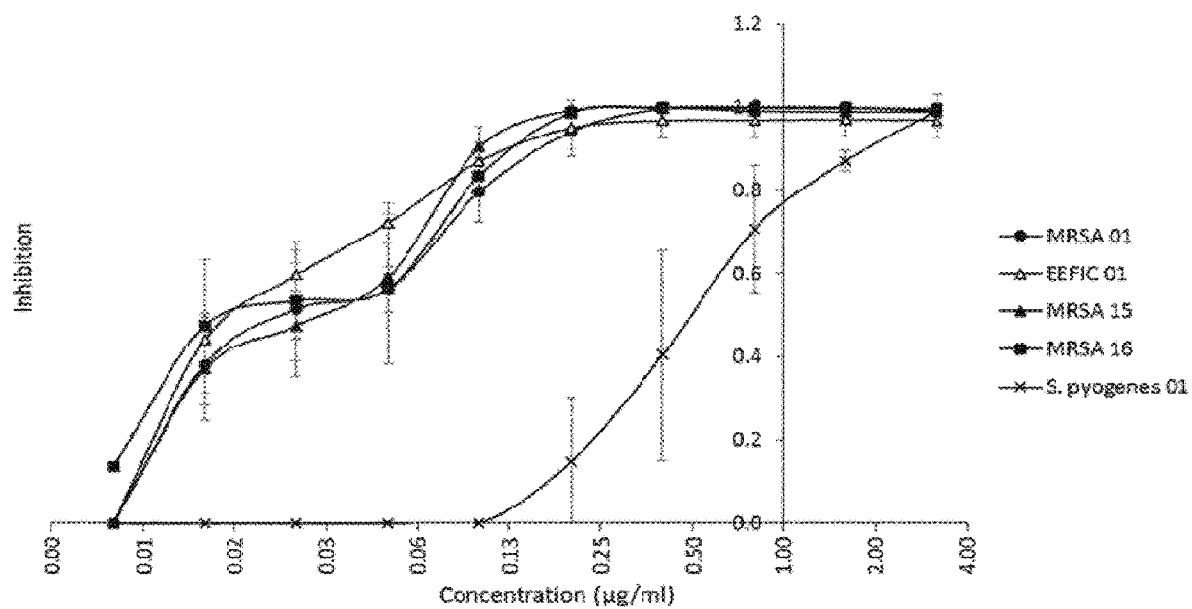

The following tests were performed to assess the antibacterial activity in vitro (FIG. 1):

1. Minimum Inhibitory Concentration (MIC) Assay

The MIC was determined using 96-well plates, and serial two-fold dilutions of niclosamide (from Sigma) (from 51.2 to 0.025 µg/ml) in above indicated medium, with 150 µl per well.

Bacterial cultures were stopped in their exponential growth phase and plates were inoculated with the approximate concentration of $10^3$ cells per well. Plates were incubated at 37° C. for 18 hours (*S. aureus*) or 24 hours (*S. pyogenes*). Optical density at a wavelength of 600 nm was measured at the end of the incubation time. Inhibition was calculated as (Inhibition=1-$OD_{test}$/$OD_{no\ treatment}$) and MIC values were determined as the minimum concentration giving 100% inhibition. Experiments were performed at least as triplicate biological replicates with all strains.

The inhibition could be either due to a bactericidal or a bacteriostatic activity, which is not known from this experiment. The following assay was thus carried out in order to determine if niclosamide kills or inhibits growth of *S. aureus*.

2. Time-Kill Assay

Assay was performed in 20 ml of medium. It included a negative control (medium without bacteria), a positive control (bacteria grown without niclosamide) and the assay (bacteria grown with niclosamide). Niclosamide was tested at 10 fold its MIC, determined in the previous experiment. This experiment was performed with the primary test microorganism indicated above.

The overnight culture was stopped and $OD_{600}$ was measured. Culture was then diluted in indicated medium to obtain an $OD_{600}$ of 0.25 in order to have about $5\times10^8$ cfu/ml. Two hundred µl of this diluted culture were then added in all conditions except in the negative control. Initial bacterial concentration was about $5\times10^6$ cfu/ml. Tubes were incubated aerobically at 37° C. for 24 hours.

Bacteria were enumerated before the incubation, after 30 minutes, 1, 2, 4, 8 and 24 hours of incubation by serial dilutions in NaCl 0.9% and plating on LB agar, with 2 plates per dilution. Plates were incubated at 37° C. and colonies enumerated after 24 hours.

The compound was considered bactericidal if the reduction of the bacterial inoculum was superior or equal to 3 $\log_{10}$ cfu/ml, bacteriostatic if reduction was inferior to 3 $\log_{10}$ cfu/ml.

3. Mutational Frequency Evaluation

The frequency of spontaneous single-step mutations was determined on 3 different strains (MRSA, fusidic acid-resistant and mupirocin-resistant) as described by Drago et al. (2005) (Drago, L., De Vecchi, E., Nicola, L., Tocalli, L., & Gismondo, M. R. (2005). In vitro selection of resistance in *Pseudomonas aeruginosa* and *Acinetobacter* spp. by levofloxacin and ciprofloxacin alone and in combination with beta-lactams and amikacin. *The Journal of Antimicrobial Chemotherapy*, 56(2), 353-359). One hundred µl of an initial inoculum of $10^9$ cfu/ml from an overnight culture were plated on LB agar plates supplemented with the test compound (0×, 1×, 2×, 4× and 10×MIC). Adequate dilutions were plated on plates without the compound.

Viable cell growth was enumerated after 48 hours of incubation at 37° C.

Ten replicates were carried out for each strain and fusidic acid, mupirocin and retapamulin were used as controls for the MRSA 01 strain.

Colony-Forming Unit (CFU) in Skin Lesions

Three animal studies were performed with niclosamide and fusidic acid as comparison with different formulations and doses.

In each experiment, female Balb/c mice received a skin lesion approximately 1 cm² and were challenged with 1.5× $10^8$ cfu MRSA 01 topically. Twenty-four hours after the wound formation and the contamination, mice were treated topically with 0.05 ml twice daily for three days. Mice were sacrificed on day 4, skin lesions were excised and cfu quantitated. Fusidin ointment (2% from Leo Pharma) was included as control.

Experiment 1

Sample 5.—Niclosamide (N) 5% modified basis creme with higher lipid content Lipocreme—according to the description in Danske Laegemiddelsstandarder (DLS).

Figure 3:
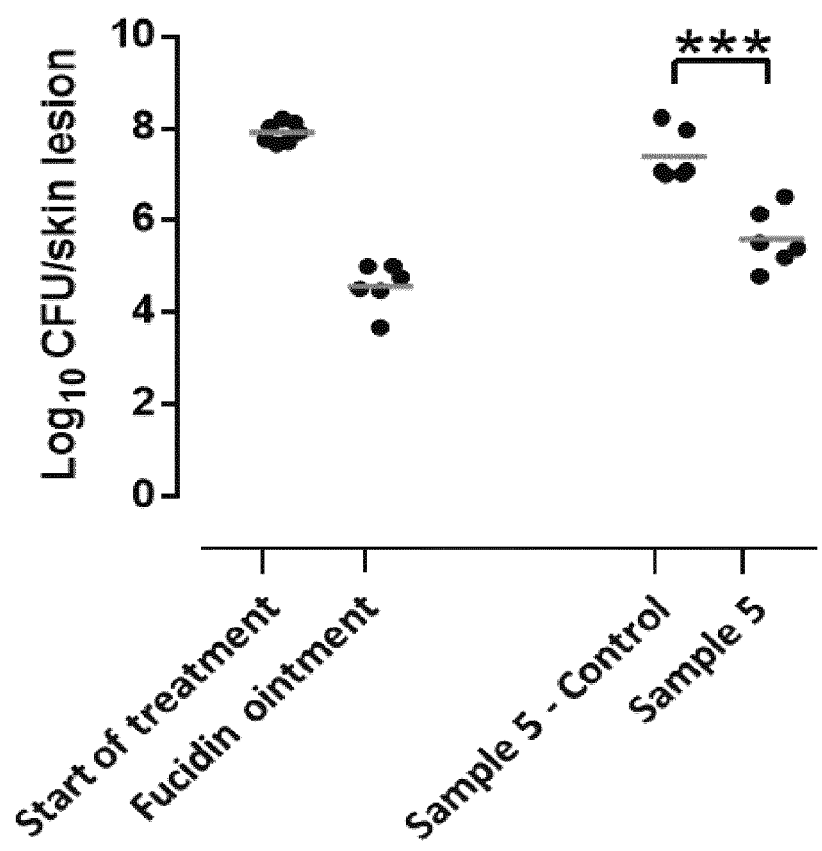
FIG. 3 shows CFU in skin lesions after three days of treatment with Samples 5. Sample-control corresponds to the sample without niclosamide *: P<0.05, unpaired t-test; : P<0.005, unpaired t-test; *: P<0.001, unpaired t-test; ns: not significant.

2.25 g niclosamide was mixed with 47.75 g creme prepared according to Danske Laegemiddels-standarder (DLS) (see FIG. 3).

| Oil phase: | Polysorbate 80 | 10 g |
|---|---|---|
| | Cetostearyl alcohol | 100 g |
| | Paraffin oil | 100 g |
| | Glycerol monostearate 40-50 | 120 g |
| Water phase: | Methyl parabenzoate | 1 g |
| | Glycerol 85% | 40 g |
| | Sorbitol | 70 g |
| | Water Milli-Q | 724 g |

Results and Conclusions

Figure 2:
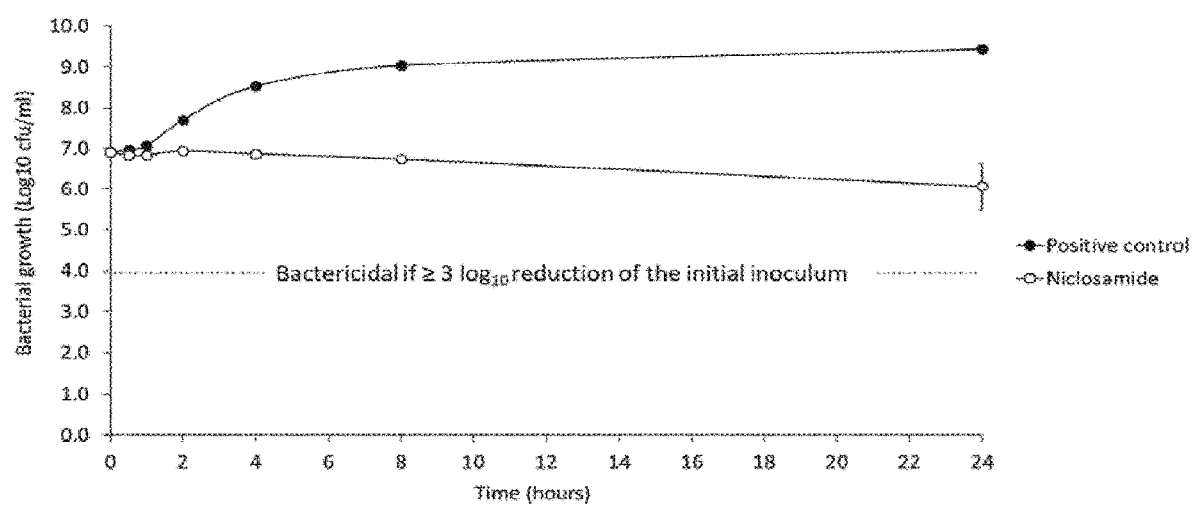
FIG. 2 shows a time-kill curve of MRSA 01 incubated with niclosamide (MIC×10). Niclosamide had a bacteriostatic effect against MRSA 01 (strain used in animal experiment) in the tested conditions (initial inoculum: 7 $\log_{10}$ cfu/ml; niclosamide: 4 μg/ml [MIC×10]).

Microbiology: MIC & Kill Curves—FIGS. 1 & 2 and Tables 2 and 3

TABLE 2 in-vitro susceptibility of *S. aureus* clinical isolates and *S. aureus* ATCC 29213 reference strain.

| | | MIC (n2/ml) |
|---|---|---|
| *S. aureus* strains | Newman | 0.2 |
| | MRSA 01 | 0.4 |
| | MRSA 02 | 0.2 |
| | MRSA 03* | 0.4 |
| | MRSA 04 | 0.4 |
| | MRSA 05 | 0.2 |
| | MRSA 06 | 0.4 |
| | MRSA 07 | 0.2 |
| | MRSA 08* | 0.4 |
| | MRSA 09 | 0.2 |
| | MRSA 10 | 0.4 |
| | MRSA 11 | 0.1 |
| | EEFIC 01* | 0.4 |
| | EEFIC 02* | 0.2 |
| | MRSA 12* | 0.4 |
| | MRSA 13* | 0.4 |

TABLE 2-continued in-vitro susceptibility of *S. aureus* clinical isolates
and *S. aureus* ATCC 29213 reference strain.

|  |  | MIC (n2/ml) |
|---|---|---|
|  | MSSA 01* | 0.4 |
|  | MSSA 02* | 0.4 |
|  | MRSA 14* | 0.4 |
|  | MRSA 15* | 0.2 |
|  | MRSA 16* | 0.2 |
|  | MRSA 17* | 0.2 |
| *S. pyogenes* strains | 01 | 3.2 |
|  | CCUG 25571 | 3.2 |
|  | ATCC 19615 | 3.2 |
|  | ATCC 12385 | 1.6 |

TABLE 3

Therapeutic indexes of halogenated salicylanilides, calculated from their MICs against *S. aureus* and *S. pyogenes* strains and their lethal Dose 50 (LD50) in rats and mice.

| Compound | Mic$_{100}$ S. aureus μg/ml | Mic$_{100}$ S. aureus μM | Mic$_{100}$ S. pyogenes μg/ml | Mic$_{100}$ S. pyogenes μM | LD$_{50}$ rats p.o (mg/kg) | LD$_{50}$ mice p.o (mg/kg) | Ther. Index (LD$_{50, rats}$/MIC$_{100, S.\ aureus}$) |
|---|---|---|---|---|---|---|---|
| Niclosamide | ≤0.4 | ≤1.25 | ≤3 | ≤3 | 5000 | >1500 | 12,500,000 |
| Closantel | ≤1.7 | ≤2.5 | 12.8‡ | 19‡ | 300 | 331 | 176,000 |
| Oxyclozanide | 1.6* | 4* | 6.4‡ | 15.9‡ | 980-3500 | 300 | 612,000-2187,000 |
| Rafoxanide | 0.8* | 1.25* | 6.4‡ | 10‡ | 1500 | 270 | 1,875,000 |

*Tested against one strain: MRSA 01
‡Tested against one strain: *S. pyogenes* 01

The data shows that halogenated salicylanilides such as closantel, oxyclozanide, rafoxanide and particularly niclosamide are strongly potent against Gram-positive strains such as *S. aureus* and *S. pyogenes*. Notably the effect is independent of the resistance profile of the isolates towards other currently used antibiotics for topical treatment of these microorganisms, including fucidic acid and mupirocin. Accordingly, the halogenated salicylanilides in general and niclosamide in particular are well suited as a possible treatment for both susceptible and resistant Gram-positive strains.

Microbiology Resistance Development—Table 4

Spontaneous mutations conferring resistance to halogenated salicylanilides occurred at a very low frequency (mutational frequency=$5\times10^{-9}$, $2\times10^{-8}$ and $1\times10^{-7}$ at MIC×1 for rafoxanide, closantel, and oxyclozanide respectively) and for niclosamide at an extremely low frequency (0≤mutational frequency<$4\times10^{-10}$ at MIC×1) compared to currently used antibiotics such as fusidic acid, retapamulin and mupirocin (mutational frequency: ≥$4\times10^{-5}$ at MIC×1) (see Table 4).

TABLE 4

Mutation rates conferring resistance to halogenated salicylanilides.

| Compound | Resistance mutation rate at MIC × 1 |
|---|---|
| Niclosamide | <$4 \times 10^{-91}$ |
| Closantel | = $2 \times 10^{-8*}$ |
| Oxyclozanide | = $1 \times 10^{-7*}$ |
| Rafoxanide | = $5 \times 10^{-9*}$ |
| Fusidic acid | ≥$4 \times 10^{-5*}$ |
| Mupirocin | ≥$4 \times 10^{-5*}$ |
| Retapamulin | ≥$4 \times 10^{-5*}$ |

1. Mutation rate conferring resistance against MRSA 01, MRSA 15 (fusidic acid-resistant) and MRSA 16 (mupirocin-resistant)
*Tested against one strain: MRSA 01

A. The mutational frequency data gives the frequency of a resistant mutant within a given population. When the mutational frequency is bellow $10^{-9}$ means that there is less than one resistant mutant in a population of $10^9$ cells.

Unexpectedly, the resistance development towards halogenated salicylanilides in general and niclosamide in particular is much slower than resistance development towards drugs like fusidic acid, mupirocin and retapamulin being on the market.

In combination, the high potency and the implementation of the low rate of resistance development makes niclosamide particularly useful for treatment, especially topical treatment of infections caused by Gram positive organisms.

In view of the unexpected microbiological findings that niclosamide has very unique properties that make it an ideal candidate as a topical anti-infective animal experiments were performed to test the effect of niclosamide in vivo.

The data described herein shows that niclosamide reduces colonization by *S. aureus* in animal model used for the tests.

In Experiment 1 (FIG. 3) niclosamide in the tested ointment and cream formulations led to significant bacterial reductions compared to the control vehicles.

In conclusion the in vivo data shows that niclosamide is well suited as a topical antibiotic for treatment of infections caused by Gram positive infections.

Example 2

Additional More Extensive Screen of Clinical Isolates Performed with Niclosamide

METHODS

Microorganisms

Chosen for its relevance regarding bacterial skin infections, the methicillin-resistant *S. aureus* (MRSA) 01 strain was used as the primary test microorganism. This strain is a community-acquired MRSA clinical isolate of USA 300 type, from a skin abscess.

Two-hundred-four other MRSA and methicillin-sensitive *S. aureus* strains, and 4 *Streptococcus pyogenes* strains, were also included in the study. These covered fusidic acid- and mupirocin-resistant strains, these two types of resistance being of clinical relevance.

Strains were conserved in Luria Bertani (LB) Broth (*S. aureus*) or Brain Heart Infusion (BHI) (*S. pyogenes*) supplemented with glycerol 15% (v/v) at −80° C., and reactivated by isolation on LB (*S. aureus*) or BHI (*S. pyogenes*) agar plates. Strains were cultivated in Mueller Hinton (MH) Broth-cation adjusted (*S. aureus*) or BHI (*S. pyogenes*). All strains were cultivated aerobically (microaerobically for *S. pyogenes* strains) at 37° C.

Antibacterial Activity

1. Minimum Inhibitory Concentration (MIC) Assay

Minimal inhibitory concentrations (MICs) of niclosamide, fusidic acid, and mupirocin were determined according to CLSI criteria with a doubling dilution concentration range (16 to 0.008 µg/ml) in Mueller Hinton Broth cation-adjusted (Fluka Analytical 90922), using 96-well plates, for 205 different *S. aureus* strains. *S. aureus* ATCC 29213 was included as a control reference strain and clindamycin and vancomycin were included as control antibiotics.

Bacterial cultures were stopped in their exponential growth phase and plates were inoculated with the approximate concentration of $5 \times 10^5$ cells per well. Plates were incubated at 37° C. for 18 hours (*S. aureus*) or 24 hours (*S. pyogenes*). Optical density at a wavelength of 600 nm was measured at the end of the incubation time Inhibition was calculated as (Inhibition=1−$OD_{test}$/$OD_{no\ treatment}$) and MIC values were determined as the minimum concentration giving 100% inhibition.

Due to interference with blood (MIC increased by 16 with 5% lysed horse blood), the MIC determination against *S. pyogenes* strains was performed in BHI.

RESULTS and DISCUSSION

In Vitro MIC Determination and Breadth of Effect

Figure 4:
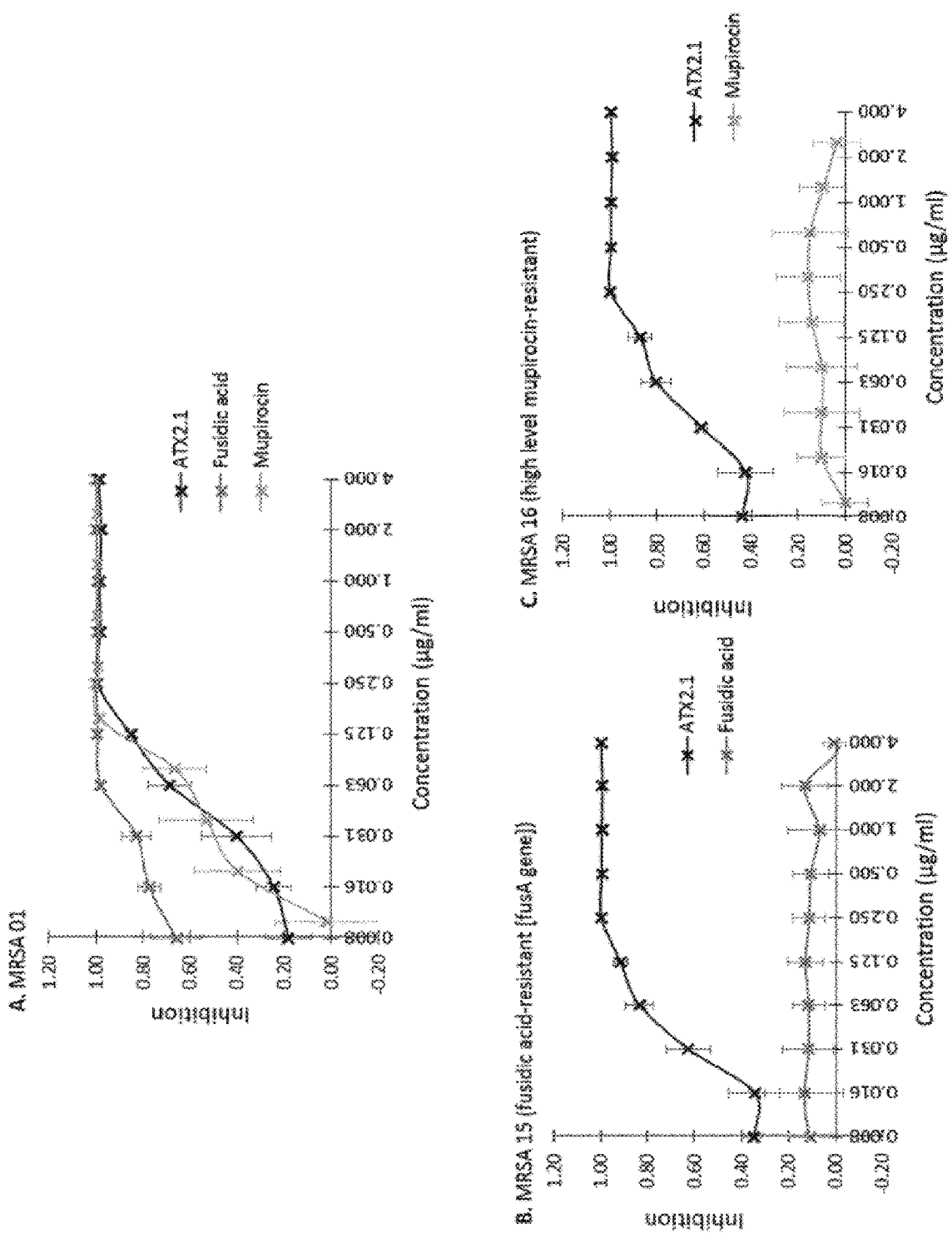
FIG. 4 shows the dose-response curves of niclosamide, fusidic acid and mupirocin against *S. aureus* with methicillin-resistant strains (A), fusidic acid-resistant strain (B) and mupirocin-resistant strain (C).

The MIC of niclosamide was ≤0.5 µg/ml against all targeted *S. aureus* and *S. pyogenes* strains, including the strains resistant to fusidic acid, mupirocin, clindamycin and retapamulin (Table 5, Table 6, Table 7 and FIG. 4). Dose-response curves of niclosamide, fusidic acid and mupirocin against *S. aureus* with different resistance profiles are represented in Figure X.

TABLE 5 in-vitro susceptibility of *S. aureus* clinical isolates and *S. aureus* ATCC 29213 reference strain.

| | MIC (µg/ml) | | | | | |
|---|---|---|---|---|---|---|
| | niclosamide | Fusidic acid | Mupirocin | Retapamulin | Clindamycin | Vancomycin |
| ATCC 29213 | 0.5 | 0.06 | 0.125 | 0.03 | 0.125 | 1 |
| Newman | 0.25 | 0.25 | 0.25 | 0.03 | 0.125 | 2 |
| MRSA 01 | 0.25 | 0.125 | 0.25 | 0.06 | 0.125 | 1 |
| MRSA 02 | 0.25 | 0.5 | 0.25 | 0.06 | 0.25 | 2 |
| MRSA 03 | 0.25 | 16 | 0.25 | 0.03 | 0.125 | 1 |
| MRSA 04 | 0.25 | 0.25 | 0.25 | 0.06 | 0.125 | 2 |
| MRSA 05 | 0.25 | 0.125 | 0.125 | 0.03 | 0.125 | 1 |
| MRSA 06 | 0.25 | 0.125 | 0.25 | 0.03 | 0.125 | 2 |
| MRSA 07 | 0.125 | 0.25 | 0.25 | 0.06 | 0.125 | 1 |
| MRSA 08 | 0.25 | 0.125 | >16 | 0.03 | >16 | 1 |
| MRSA 09 | 0.125 | 0.25 | 0.25 | 0.06 | 0.25 | 2 |
| MRSA 10 | 0.25 | 1 | 0.25 | 0.06 | 0.25 | 1 |
| MRSA 11 | 0.25 | 1 | 0.5 | 0.06 | >16 | 1 |
| EEFIC 01 | 0.25 | 4 | 0.125 | 0.03 | 0.125 | 1 |
| EEFIC 02 | 0.25 | 4 | 0.125 | 0.03 | 0.125 | 1 |
| MRSA 12 | 0.5 | 4 | 0.125 | 0.03 | ND | ND |
| MRSA 13 | 0.25 | 4 | 0.25 | 0.06 | 0.125 | 1 |
| MSSA 01 | 0.5 | 4 | 0.125 | 0.03 | 0.125 | 1 |
| MSSA 02 | 0.25 | 4 | 0.125 | 0.03 | 0.125 | 1 |
| MRSA 14 | 0.25 | >16 | 0.125 | 0.03 | >16 | 1 |
| MRSA 15 | 0.25 | >16 | 0.25 | 0.06 | 0.125 | 2 |
| MRSA 16 | 0.25 | 0.25 | >16 | 0.06 | 0.25 | 1 |
| MRSA 17 | 0.25 | 4 | >16 | 0.03 | >16 | 2 |
| MRSA 18 | 0.25 | 0.25 | 0.125 | 0.06 | 0.125 | 1 |
| MRSA 19 | 0.25 | 0.125 | 0.25 | 0.03 | 0.125 | 1 |
| MRSA 20 | 0.25 | 0.125 | 0.25 | 0.06 | 0.06 | 1 |
| MRSA 21 | 0.25 | 0.125 | 0.125 | 0.125 | 0.03 | 1 |
| MRSA 22 | 0.25 | >16 | 0.25 | 0.06 | 0.06 | 0.5 |
| MRSA 23 | 0.25 | 0.25 | 0.25 | 0.06 | 0.125 | 1 |
| MRSA 24 | 0.25 | 0.25 | 0.25 | 0.06 | 0.125 | 2 |
| MRSA 25 | 0.25 | 16 | 0.25 | 0.06 | 0.125 | 1 |
| MRSA 26 | 0.5 | 0.5 | 0.5 | 0.06 | >16 | 1 |
| MRSA 27 | 0.5 | 0.25 | 0.25 | 0.06 | 0.125 | 1 |
| MRSA 28 | 0.25 | 0.06 | 0.5 | 0.03 | 0.06 | 1 |
| MRSA 29 | 0.5 | 4 | 0.25 | 0.06 | 0.125 | 1 |
| MRSA 30 | 0.25 | 0.125 | 0.125 | 0.03 | 0.06 | 1 |
| MRSA 31 | 0.25 | 0.25 | 0.25 | 16 | >16 | 1 |
| MRSA 32 | 0.25 | 0.5 | 0.25 | 0.06 | 0.125 | 1 |
| MRSA 33 | 0.25 | 0.5 | 0.25 | 0.06 | 0.125 | 1 |

TABLE 5-continued in-vitro susceptibility of S. aureus clinical isolates
and S. aureus ATCC 29213 reference strain.

|  | MIC (µg/ml) | | | | | |
| --- | --- | --- | --- | --- | --- | --- |
|  | niclosamide | Fusidic acid | Mupirocin | Retapamulin | Clindamycin | Vancomycin |
| MRSA 34 | 0.25 | 0.25 | 0.25 | 0.06 | 0.125 | 1 |
| MRSA 35 | 0.25 | 16 | 0.5 | 0.03 | >16 | 1 |
| MRSA 36 | 0.25 | 8 | 0.25 | 0.06 | 0.06 | 1 |
| MRSA 37 | 0.25 | 0.5 | 0.25 | 0.06 | 0.125 | 1 |
| MRSA 38 | 0.25 | 8 | 0.125 | 0.06 | 0.125 | 1 |
| MRSA 39 | 0.25 | 8 | 0.25 | 0.06 | 0.06 | 1 |
| MRSA 40 | 0.25 | 0.125 | 0.25 | 0.03 | 0.06 | 1 |
| MRSA 41 | 0.25 | >16 | 0.125 | 0.02 | 0.06 | 1 |
| MRSA 42 | 0.25 | 0.25 | 0.25 | 0.06 | >16 | 1 |
| MRSA 43 | 0.25 | 0.125 | 0.25 | 0.06 | 0.06 | 1 |
| MRSA 44 | 0.25 | 4 | 0.25 | 0.02 | 0.03 | 1 |
| MRSA 45 | 0.25 | 0.06 | 0.13 | 0.02 | 0.06 | 1 |
| MRSA 46 | 0.25 | 0.06 | 0.13 | 0.02 | 0.03 | 1 |
| MRSA 47 | 0.25 | 0.06 | 0.25 | 0.02 | >16 | 0.5 |
| MRSA 48 | 0.25 | 2 | 0.13 | 0.02 | 0.03 | 0.5 |
| MRSA 49 | 0.25 | 0.25 | 0.25 | 0.02 | 0.03 | 2 |
| MRSA 50 | 0.25 | 0.03 | 0.25 | 0.02 | 0.02 | 1 |
| MRSA 51 | 0.125 | 0.13 | 0.25 | 0.03 | 0.06 | 1 |
| MRSA 52 | 0.25 | 0.06 | 0.25 | 0.02 | 0.03 | 1 |
| MRSA 53 | 0.25 | 0.25 | 0.25 | 0.03 | 0.06 | 1 |
| MRSA 54 | 0.25 | 0.125 | 0.25 | 0.03 | 0.06 | 2 |
| MRSA 55 | 0.25 | 4 | 0.25 | 0.02 | 0.03 | 0.5 |
| MRSA 56 | 0.25 | 0.06 | 0.25 | <0.01 | 0.03 | 1 |
| MRSA 57 | 0.25 | 0.125 | 0.125 | 0.02 | 0.03 | 1 |
| MRSA 58 | 0.25 | 4 | 0.125 | 0.02 | 0.06 | 1 |
| MRSA 59 | 0.25 | 0.06 | 0.125 | 0.02 | 0.03 | 1 |
| MRSA 60 | 0.25 | 8 | 0.25 | 0.02 | 0.06 | 0.5 |
| MRSA 61 | 0.25 | 0.06 | 0.25 | 0.02 | 0.03 | 2 |
| MRSA 62 | 0.25 | 0.06 | 0.25 | 0.02 | 0.06 | 2 |
| MRSA 63 | 0.25 | 0.125 | 0.125 | 0.02 | 0.06 | 1 |
| MRSA 64 | 0.25 | 0.25 | 0.25 | 0.02 | 0.06 | 1 |
| MRSA 65 | 0.25 | 0.06 | 0.25 | 0.02 | 0.03 | 1 |
| MRSA 66 | 0.25 | 0.06 | 0.25 | 0.02 | 0.03 | 1 |
| MRSA 67 | 0.25 | 0.25 | 0.125 | 0.02 | 0.03 | 1 |
| MRSA 68 | 0.25 | 0.125 | 0.25 | 0.02 | 0.03 | 1 |
| MRSA 69 | 0.25 | 4 | 0.125 | <0.01 | 0.03 | 1 |
| MRSA 70 | 0.125 | 8 | 0.25 | 0.02 | 0.06 | 1 |
| MRSA 71 | 0.25 | 0.06 | 0.125 | <0.01 | 0.02 | 1 |
| MRSA 72 | 0.25 | 16 | 0.25 | 0.03 | 0.06 | 1 |
| MRSA 73 | 0.5 | 0.25 | 0.25 | 0.03 | 0.125 | 1 |
| MRSA 74 | 0.25 | 0.25 | 0.25 | 0.03 | 0.125 | 2 |
| MRSA 75 | 0.5 | 0.5 | 0.5 | 0.03 | 0.125 | 1 |
| MRSA 76 | 0.25 | 0.25 | 0.25 | 0.03 | 0.125 | 1 |
| MRSA 77 | 0.25 | 16 | 0.25 | 0.03 | 0.125 | 2 |
| MRSA 78 | 0.5 | 0.125 | 0.25 | 0.03 | 0.06 | 1 |
| MRSA 79 | 0.25 | 0.5 | 0.25 | <0.01 | 0.03 | 1 |
| MRSA 80 | 0.5 | 0.125 | 0.25 | 0.02 | 0.06 | 1 |
| MRSA 81 | 0.5 | 0.25 | 0.25 | 0.03 | 0.125 | 1 |
| MRSA 82 | 0.25 | 8 | 0.25 | 0.03 | 0.125 | 2 |
| MRSA 83 | 0.5 | 0.06 | 0.25 | 0.03 | 0.06 | 1 |
| MRSA 27b | 0.25 | 8 | 0.25 | 0.02 | 0.06 | 1 |
| MRSA 84 | 0.25 | 8 | 0.25 | 0.03 | 0.125 | 2 |
| MRSA 85 | 0.5 | 4 | 0.25 | 0.03 | 0.125 | 1 |
| MRSA 86 | 0.25 | >16 | 0.25 | 0.03 | 0.06 | 2 |
| MRSA 87 | 0.25 | 0.125 | 0.25 | 0.02 | 0.06 | 1 |
| MRSA 88 | 0.25 | 0.06 | 0.25 | 0.03 | 0.06 | 1 |
| MRSA 89 | 0.5 | 0.06 | 0.25 | 0.02 | >16 | 1 |
| MRSA 90 | 0.5 | 16 | 0.25 | 0.06 | 0.125 | 1 |
| MRSA 91 | 0.25 | 0.25 | 0.25 | 0.06 | 0.125 | 1 |
| MRSA 92 | 0.25 | 8 | 0.25 | 0.06 | 0.06 | 1 |
| MRSA 93 | 0.25 | 0.02 | 0.25 | 0.02 | 0.03 | 2 |
| MRSA 94 | 0.25 | 0.125 | 0.25 | 0.03 | 0.125 | 2 |
| MRSA 95 | 0.25 | 8 | 0.25 | 0.03 | 0.125 | 2 |
| MRSA 96 | 0.25 | 0.125 | 0.125 | 0.03 | >16 | 1 |
| MRSA 97 | 0.25 | 8 | 0.25 | 0.03 | 0.06 | 1 |
| MRSA 98 | 0.5 | 0.06 | 0.5 | 0.03 | >16 | 1 |
| MRSA 99 | 0.25 | 0.125 | 0.5 | 0.03 | 0.125 | 1 |
| MRSA 100 | 0.25 | 0.125 | 0.5 | 1 | 0.25 | 1 |
| MRSA 101 | 0.5 | 8 | 0.25 | 0.03 | 0.06 | 1 |
| MRSA 102 | 0.25 | 0.06 | 0.25 | 0.03 | 0.06 | 2 |
| MRSA 103 | 0.25 | 8 | 0.25 | 0.03 | 0.125 | 1 |
| MRSA 104 | 0.5 | 0.25 | 0.25 | 0.03 | 0.125 | 1 |
| MRSA 105 | 0.25 | 0.125 | 0.25 | 0.03 | 0.125 | 1 |

TABLE 5-continued in-vitro susceptibility of S. aureus clinical isolates
and S. aureus ATCC 29213 reference strain.

| | MIC (µg/ml) | | | | | |
|---|---|---|---|---|---|---|
| | niclosamide | Fusidic acid | Mupirocin | Retapamulin | Clindamycin | Vancomycin |
| MRSA 106 | 0.25 | 0.125 | 0.25 | 0.06 | 0.125 | 1 |
| MRSA 107 | 0.25 | 0.25 | 0.25 | 0.06 | 0.125 | 2 |
| MRSA 108 | 0.25 | 4 | 0.25 | 0.03 | 0.125 | 1 |
| MRSA 109 | 0.25 | 0.25 | 0.25 | 0.03 | 0.125 | 1 |
| MRSA 110 | 0.25 | 0.06 | 0.125 | 0.03 | 0.125 | 1 |
| MRSA 111 | 0.5 | 8 | 0.25 | 0.03 | 0.125 | 1 |
| MRSA 112 | 0.25 | 0.06 | 0.25 | 0.03 | 0.06 | 1 |
| MRSA 113 | 0.25 | 0.125 | 0.25 | 0.03 | 0.06 | 1 |
| K000796 | 0.25 | 8 | 0.5 | 0.03 | 0.125 | 1 |
| K115688 | 0.25 | 0.125 | 0.25 | 0.03 | 0.125 | 2 |
| K000866 | 0.25 | 8 | 0.5 | 0.03 | 0.125 | 1 |
| K000864 | 0.25 | 0.25 | 0.25 | 0.03 | 0.125 | 1 |
| K000863 | 0.25 | 1 | 0.5 | 0.03 | 0.125 | 1 |
| K115689 | 0.25 | 0.125 | 0.25 | 0.03 | 0.125 | 2 |
| K000772 | 0.25 | >16 | 0.125 | 0.06 | 0.125 | 1 |
| K115498 | 0.25 | 0.125 | 0.5 | 0.03 | 0.125 | 2 |
| R000024 | 0.25 | 16 | 0.5 | 0.06 | 0.125 | 1 |
| R000020 | 0.5 | 0.125 | 0.5 | 0.03 | 0.125 | 1 |
| R000019 | 0.5 | 0.125 | 0.5 | 0.06 | 0.125 | 2 |
| U115579 | 0.25 | 0.25 | 0.5 | 0.06 | 0.125 | 1 |
| 115370U | 0.25 | 0.5 | 0.125 | 0.06 | 0.125 | 1 |
| 114660U | 0.25 | 0.25 | 0.25 | 0.06 | 0.125 | 1 |
| 115584D | 0.25 | 0.25 | 0.5 | 0.06 | 0.125 | 2 |
| 115740E | 0.5 | 0.25 | 0.25 | 0.06 | 0.125 | 1 |
| 115810E | 0.25 | 0.25 | 0.25 | 0.06 | 0.125 | 1 |
| 115628T | 0.25 | 8 | 0.25 | 0.03 | 0.06 | 2 |
| 000274T | 0.25 | 0.5 | 0.5 | 0.06 | 0.125 | 1 |
| 115691T | 0.5 | 0.25 | 0.25 | 0.03 | 0.125 | 1 |
| 115903T | 0.5 | 8 | 0.5 | 0.03 | 0.125 | 1 |
| 116122T | 0.25 | 0.125 | 0.5 | 0.03 | 0.125 | 1 |
| 115015T | 0.5 | 0.25 | 0.5 | 0.06 | 0.125 | 2 |
| 115273C | 0.5 | 0.25 | 0.25 | 0.03 | 0.125 | 1 |
| 000040C | 0.5 | 0.25 | 0.25 | 0.03 | 0.125 | 1 |
| 115690C | 0.25 | 8 | 0.125 | 0.25 | 0.5 | 2 |
| 115561C | 0.25 | 0.125 | 0.5 | 0.03 | 0.125 | 1 |
| 115445C | 0.5 | 0.25 | 0.25 | 0.03 | 0.125 | 1 |
| 115263C | 0.25 | 0.125 | 0.25 | 0.03 | 0.06 | 2 |
| 115303C | 0.5 | 0.25 | 0.25 | 0.03 | >16 | 1 |
| 115268C | 0.5 | 0.25 | 0.5 | 0.03 | 0.125 | 1 |
| 115295C | 0.25 | 0.125 | 0.25 | 0.03 | 0.125 | 1 |
| 115242C | 0.5 | 8 | 0.25 | 0.03 | 0.06 | 1 |
| 115427C | 0.25 | 0.125 | 0.25 | 0.03 | 0.06 | 1 |
| 000041C | 0.25 | 0.25 | 0.25 | 0.03 | 0.06 | 1 |
| E5-1048654 | 0.25 | 0.5 | 0.25 | 0.06 | 0.125 | 1 |
| 9-2955245 | 0.25 | 0.25 | 0.25 | 0.06 | 0.125 | 1 |
| E5-1046019 | 0.25 | 0.25 | 0.25 | 0.03 | 0.125 | 1 |
| E5-1046020 | 0.5 | 0.25 | 0.25 | 0.06 | 0.125 | 1 |
| E5-1047585 | 0.25 | 0.25 | 0.25 | 0.03 | 0.125 | 1 |
| E5-1038294 | 0.5 | 0.25 | 0.25 | 0.03 | 0.125 | 1 |
| E5-1035779 | 0.5 | 0.125 | 0.5 | 0.03 | 0.125 | 1 |
| 9-1862936 | 0.5 | 0.125 | 0.25 | 0.03 | 0.125 | 1 |
| E5-1033091 | 0.5 | 0.03 | 0.25 | 0.02 | 0.06 | 1 |
| 9-26422166 | 0.5 | 8 | 0.25 | 0.03 | 0.125 | 1 |
| 9-2642158 | 0.25 | 0.25 | 0.25 | 0.06 | 0.125 | 1 |
| E5-1035775 | 0.5 | >16 | 0.25 | 0.06 | 0.125 | 1 |
| E5-1029558 | 0.25 | 16 | 0.5 | 0.03 | 0.125 | 1 |
| E5-1038279 | 0.5 | 4 | 0.25 | 0.03 | 0.125 | 1 |
| E5-1039697 | 0.25 | 0.5 | 0.25 | 0.06 | 0.125 | 1 |
| E5-1041979 | 0.5 | 0.25 | 0.5 | 0.03 | 0.125 | 1 |
| E5-1035284 | 0.25 | 0.25 | 0.25 | 0.03 | 0.125 | 1 |
| E5-1030469 | 0.25 | 0.125 | 0.25 | 0.03 | 0.125 | 2 |
| E5-1030472 | 0.5 | 0.25 | 0.5 | 0.06 | 0.125 | 1 |
| E5-1041977 | 0.5 | 16 | 0.5 | 0.03 | 0.125 | 2 |
| E5-1041987 | 0.5 | 16 | 0.25 | 0.03 | 0.125 | 1 |
| E5-1039684 | 0.5 | 16 | 0.25 | 0.06 | 0.125 | 1 |
| E5-1041980 | 0.25 | 0.25 | 0.25 | 0.03 | 0.125 | 1 |
| E5-1033088 | 0.25 | 0.25 | 0.25 | 0.03 | 0.125 | 1 |
| E5-1035277 | 0.5 | 16 | 0.5 | 0.03 | 0.125 | 1 |
| E5-1046096 | 0.5 | 0.5 | 0.5 | 0.06 | 0.125 | 1 |
| E5-1046085 | 0.5 | 8 | 0.5 | 0.06 | 0.125 | 2 |
| 9-2625962 | 0.5 | 0.25 | 0.5 | 0.03 | 0.125 | 1 |
| E5-1043668 | 0.25 | 1 | 0.25 | 0.06 | 0.25 | 1 |
| E5-1048428 | 0.25 | 0.5 | 0.25 | 0.06 | 0.25 | 1 |

TABLE 5-continued in-vitro susceptibility of S. aureus clinical isolates
and S. aureus ATCC 29213 reference strain.

| | MIC (µg/ml) | | | | | |
|---|---|---|---|---|---|---|
| | niclosamide | Fusidic acid | Mupirocin | Retapamulin | Clindamycin | Vancomycin |
| E5-1047924 | 0.5 | 0.25 | 0.5 | 0.03 | 0.125 | 1 |
| E5-1047606 | 0.5 | 8 | 0.5 | 0.03 | 0.125 | 1 |
| E5-1046070 | 0.25 | 0.25 | 0.5 | 0.03 | 0.125 | 1 |
| E5-1046298 | 0.25 | 0.125 | 0.25 | 0.03 | 0.125 | 1 |
| E5-1046296 | 0.5 | 0.125 | 1 | 0.03 | 0.125 | 1 |
| E5-1046297 | 0.5 | 0.125 | 0.25 | 0.06 | 0.125 | 1 |
| E5-1043184 | 0.5 | 16 | 0.5 | 0.03 | 0.125 | 1 |
| E5-1038286 | 0.25 | 0.25 | 0.5 | 0.06 | 0.125 | 1 |
| E5-1037958 | 0.5 | 16 | 0.5 | 0.06 | 0.125 | 1 |
| E5-1037971 | 0.25 | 0.25 | 0.25 | 0.03 | 0.125 | 1 |
| E5-1033076 | 0.5 | 0.25 | 0.25 | 0.03 | 0.125 | 1 |
| E5-1033076 | 0.5 | 0.25 | 0.25 | 0.03 | 0.125 | 1 |
| E5-1029252 | 0.25 | 0.25 | 0.5 | 0.03 | 0.125 | 1 |
| E5-1030440 | 0.25 | 0.25 | 0.25 | 0.06 | 0.06 | 1 |
| E5-1030482 | 0.125 | 16 | 0.25 | 0.02 | 0.06 | 1 |
| E5-1046074 | 0.25 | 0.125 | 0.25 | 0.06 | 0.125 | 1 |
| E5-1048204 | 0.25 | 0.25 | 0.25 | 0.03 | 0.06 | 2 |
| E5-1048670 | 0.125 | 0.5 | 0.5 | 0.06 | 0.125 | 2 |
| E5-1046039 | 0.25 | 0.25 | 0.25 | 0.06 | 0.125 | 1 |
| E5-1045179 | 0.25 | 0.25 | 0.25 | 0.06 | 0.125 | 1 |
| E5-1046723 | 0.25 | 0.5 | 0.25 | 0.06 | 0.125 | 2 |

Resistances are indicated in Bold.
ND: not determined.

TABLE 6

MIC distribution of niclosamide against Staphylococcus aureus
and Streptococcus pyogenes strains (percentage and ratio)

| MIC (µg/ml) | 0.0625 | 0.125 | 0.25 | 0.5 |
|---|---|---|---|---|
| Staphylococcus aureus strains | | 3% (6/205) | 70% (144/205) | 27% (55/205) |
| Streptococcus pyogenes strains | 25% (1/4) | 25% (1/4) | 25% (1/4) | 25% (1/4) |

TABLE 7

MIC90, MIC50 and MIC ranges of
niclosamide for Staphylococcus aureus strains.

| MIC90 | MIC50 | Range values |
|---|---|---|
| 0.5 µg/ml | 0.25 µg/ml | 0.125-0.5 µg/ml |

Niclosamide was inhibitory at a concentration equal or below 0.5 µg/ml. for all targeted S. aureus and S. pyogenes strains, including fusidic acid- and mupirocin-resistant strains.

Example 3

A further study was carried out to examine the frequency of spontaneous mutation conferring resistance to niclosamide in 3 methicillin-resistant Staphylococcus aureus strains, including a fusidic acid- and a mupirocin-resistant strains. This frequency was compared with the frequencies of spontaneous mutation conferring resistance to fusidic acid, mupirocin and retapamulin in one MRSA strain.

METHODS

Microorganisms

Three methicillin-resistant Staphylococcus aureus (MRSA) clinical isolates, with different resistance profiles (MRSA 01, MRSA15 [fusidic acid-resistant strain] and MRSA 16 [mupirocin-resistant strain]) were chosen for their relevance regarding bacterial skin infections The MRSA 01 strain was used as the primary test microorganism. This strain is a community-acquired MRSA clinical isolate of USA 300 type, from a skin abscess.

Strains were conserved in Luria Bertani (LB) Broth supplemented with glycerol 15% (v/v) at −80° C., and reactivated by isolation on LB agar plates. Strains were cultivated aerobically in Mueller Hinton (MH) Broth-cation adjusted at 37° C.

Mutational Frequency Evaluation

The frequency of spontaneous single-step mutations was determined on the 3 different strains as described by Drago et al. (2005) and Pannu et al. (2011). One hundred µl of an initial inoculum of about $10^9$ cfu/ml from an overnight culture were plated on LB agar plates supplemented with the test compound (0×, 1×, 2×, 4× and 10× MIC). Adequate dilutions were plated on plates without the compound.

Viable cell growth was enumerated after 48 hours of incubation at 37° C.

The spontaneous resistance frequency for an isolate-drug combination was calculated from the number of colonies that grew on plates containing drug versus the number of colonies that grew on drug-free agar.

Ten replicates were carried out for each strain and fusidic acid, mupirocin and retapamulin were used as controls for the MRSA 01 strain.

RESULTS and DISCUSSION

Spontaneous mutations conferring resistance to niclosamide occurred at an extremely low frequency (below the detection limit) (0≤mutational frequency<$4.10^{-9}$ at MIC×1) for all tested strains (MRSA 01, MRSA 15 (fusidic acid-resistant) and MRSA 16 (mupirocin-resistant)) compared to fusidic acid (mutational frequency: $3.10^{-7}$ at MIC×10 and ≥$4.10^{-5}$ at MIC×1) and to mupirocin and retapamulin. Results with the strain MRSA 01 are shown in Table 8.

Table 8

Frequencies of spontaneous mutations conferring resistance to niclosamide, fusidic acid, mupirocin and retapamulin with the strain MRSA 01. Average of 10 replicates.

|  |  | Niclosamide | Fusidic acid | Mupirocin | Retapamulin |
|---|---|---|---|---|---|
| Concentration | MIC × 1 | <4 × $10^{-9}$* | ≥$4.10^{-5}$ | ≥$4.10^{-5}$ | ≥$4.10^{-5}$ |
|  | MIC × 2 | <4 × $10^{-9}$* | $2.10^{-5}$ | $8.10^{-8}$ | $3.10^{-7}$ |
|  | MIC × 4 | <4 × $10^{-9}$* | $1.10^{-6}$ | $1.10^{-8}$ | $2.10^{-8}$ |
|  | MIC × 10 | <4 × $10^{-9}$* | $3.10^{-7}$ | ≤$4.10^{-9}$ | <$4.10^{-9}$* |

*: Below the detection limit (no colony on plates)

As for MRSA 01, no colony grew on plates with niclosamide with the strains MRSA 15 and MRSA 16. These led to a mutation frequency<$3 \times 10^{-8}$ for MRSA 15 and <$1 \times 10^{-7}$ for MRSA 16 at MIC×1 (0.25 µg/ml), these differences in the detection limits being due to differences in the bacterial concentrations of overnight cultures.

CONCLUSIONS

Frequencies of spontaneous mutations conferring resistance to niclosamide in *Staphylococcus aureus* were much lower than frequencies of spontaneous mutations conferring resistance to fusidic acid, mupirocin and retapamulin in *Staphylococcus aureus*. This supports the use of niclosamide for cutaneous decolonization of *S. aureus*.

Example 4

A study was carried out to determine the effect of pH on the antibacterial activity of niclosamide against *Staphylococcus aureus* in order to assess whether niclosamide is still active against *S. aureus* at pH close to the pH of the skin.

METHODS

Microorganisms

Chosen for its relevance regarding bacterial skin infections, the methicillin-resistant *S. aureus* (MRSA) 01 strain was used. This strain is a community-acquired MRSA clinical isolate of USA 300 type, from a skin abscess.

This strain was conserved in Luria Bertani (LB) Broth supplemented with glycerol 15% (v/v) at −80° C., and reactivated by isolation on LB agar plates. It was then cultivated aerobically in Mueller Hinton (MH) Broth-cation adjusted at 37° C.

Assessment of the Effect of pH on the Antibacterial Activity of Niclosamide

The pH of Mueller-Hinton Broth cation-adjusted was adjusted with HCl 2M to 7, 6.5, 6, 5.5, 5, 4.5 and 5. Ten ml of medium for each pH were prepared. pH of non-adjusted MHBII was equal to 7.4.

Each pH-adjusted samples were filtered on 0.2 µm filters before being used for the MIC determination assay. For each pH, minimal inhibitory concentrations (MICs) of niclosamide were determined according to CLSI criteria with a doubling dilution concentration range (16 to 0.008 µg/ml).

Bacterial culture was stopped in its exponential growth phase and plates were inoculated with the approximate concentration of $5 \times 10^5$ cells per well. Plates were incubated at 37° C. for 18 hours (*S. aureus*). Optical density at a wavelength of 600 nm was measured at the end of the incubation time Inhibition was calculated as (Inhibition=1− $OD_{test}/OD_{no\ treatment}$) and MIC values were determined as the minimum concentration giving 100% inhibition.

The experiment was performed in triple biological replicates.

RESULTS and DISCUSSION

The pH of different pH-adjusted media were checked after the addition of niclosamide in order to check that the addition of niclosamide did not have any influence on the pH. Measurements showed that the addition of niclosamide (16 µg/ml) in the pH-adjusted media had no influence on the pH (Table 9).

MRSA 01 grew equally well from pH 6 to pH 7.4 ($OD_{600} \approx 0.2$ in average in positive control wells) and slightly less in pH 5.5 ($OD_{600} \approx 0.1$ in average in positive control wells). However, the strain was inhibited by the lowest pH (pH 4 to pH 5) (FIG. 5).

MIC determinations showed that the inhibitory activity of niclosamide against MRSA 01 was increased when pH was decreased, with lower MICs (Table 9).

TABLE 9 pH and related MICs of niclosamide against MRSA 01 with the 3 different replicates.

|  | Replicate 1 | | | Replicate 2 | | Replicate 3 | |
|---|---|---|---|---|---|---|---|
|  | actual pH | pH after addition of niclosamide | MIC (µg/ml) | actual pH | MIC (µg/ml) | actual pH | MIC (µg/ml) |
| Not adjusted | 7.4 | 7.4 | 0.5 | 7.4 | 0.25 | 7.4 | 0.5 |
| pH 7.0 | 6.921 | 6.938 | 0.25 | 7.071 | 0.125 | 7.025 | 0.125 |
| pH 6.5 | 6.512 | 6.543 | 0.125 | 6.566 | 0.06 | 6.540 | 0.03 |
| pH 6.0 | 5.893 | 5.954 | 0.06 | 5.955 | 0.06 | 5.980 | 0.016 |
| pH 5.5 | 5.569 | 5.616 | ≤0.03 | 5.547 | ≤0.008 | 5.530 | ≤0.008 |
| pH 5.0 | 5.070 | 5.095 | No growth in positive | 5.068 | No growth in positive | 5.008 | No growth in positive |
| pH 4.5 | 4.569 | 4.589 | | 4.568 | | 4.550 | |

TABLE 9-continued pH and related MICs of niclosamide against MRSA 01 with the 3 different replicates.

| | Replicate 1 | | | Replicate 2 | | Replicate 3 | |
|---|---|---|---|---|---|---|---|
| | actual pH | pH after addition of niclosamide | MIC (µg/ml) | actual pH | MIC (µg/ml) | actual pH | MIC (µg/ml) |
| pH 4.0 | 4.076 | 4.105 | control. Strain inhibited by acidic pH | 4.044 | control. Strain inhibited by acidic pH | 4.023 | control. Strain inhibited by acidic pH |
| Initial bacterial concentration | | 2.E+05 cfu/ml | | 2.E+05 cfu/ml | | 3.E+05 cfu/ml | |

CONCLUSIONS

The maximal inhibitory effect of niclosamide was observed at pH 5.5, which is close to the pH of the skin.

The invention claimed is:

1. A method of ameliorating a symptom of atopic dermatitis in a human subject, the method comprising topically administering to an area of skin of the subject affected by atopic dermatitis a pharmaceutical formulation comprising an effective amount of niclosamide or a pharmaceutically salt thereof.

2. The method of claim 1, wherein the pharmaceutical formulation comprises from 2 to 10% (w/w) of niclosamide or a pharmaceutically acceptable salt thereof.

3. The method of claim 1, wherein the pharmaceutical formulation comprises from 3 to 8% (w/w) of niclosamide or a pharmaceutically acceptable salt thereof.

4. The method of claim 1, wherein the pharmaceutical formulation comprises from 4 to 6% (w/w) of niclosamide or a pharmaceutically acceptable salt thereof.

5. The method of claim 1, wherein the pharmaceutical formulation comprises niclosamide.

6. The method of claim 1, wherein the pharmaceutical formulation is administered at least once per day.

* * * * *